United States Patent
Vaidya et al.

(10) Patent No.: US 12,310,736 B1
(45) Date of Patent: May 27, 2025

(54) APPARATUS AND METHODS FOR IDENTIFYING ABNORMAL BIOMEDICAL FEATURES WITHIN IMAGES OF BIOMEDICAL DATA

(71) Applicant: Anumana, Inc., Cambridge, MA (US)

(72) Inventors: Suthirth Vaidya, Bengaluru (IN); Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/653,235

(22) Filed: May 2, 2024

(51) Int. Cl.
*A61B 5/339* (2021.01)
*A61B 5/00* (2006.01)

(52) U.S. Cl.
CPC ............ *A61B 5/339* (2021.01); *A61B 5/7475* (2013.01)

(58) Field of Classification Search
CPC ................................ A61B 5/346; A61B 5/339
See application file for complete search history.

(56) References Cited

U.S. PATENT DOCUMENTS

| | | | |
|---|---|---|---|
| 7,949,167 B2 | 5/2011 | Krishnan et al. | |
| 8,144,963 B2 | 3/2012 | Cascio et al. | |
| 11,244,755 B1 | 2/2022 | Syeda-Mahmood et al. | |
| 2019/0021677 A1* | 1/2019 | Grbic | G06T 7/11 |
| 2023/0397889 A1* | 12/2023 | Zhang | A61B 5/7267 |

* cited by examiner

*Primary Examiner* — George R Evanisko
(74) *Attorney, Agent, or Firm* — Caldwell Intellectual Property Law

(57) ABSTRACT

Apparatus for identification of abnormal biomedical features within images of biomedical data and methods used therein are described. The apparatus includes an image capture device, a processor connected to the image capture device, a memory connected to the processor, and a display device connected to the processor. The image capture device is configured to capture an image of biomedical data. The memory contains instructions configuring the processor to receive the image, extract a plurality of biomedical features from the biomedical data, receive repository data from a medical repository as a function of the plurality of biomedical features, generate at least a distance metric as a function of the plurality of biomedical features and the repository data, and highlight at least a biomedical feature within the image as a function of the at least a distance metric.

20 Claims, 19 Drawing Sheets

------ 916
——— 920
········ 924

------ 916
——— 920
········ 924

APPARATUS AND METHODS FOR IDENTIFYING ABNORMAL BIOMEDICAL FEATURES WITHIN IMAGES OF BIOMEDICAL DATA

FIELD OF THE INVENTION

The present invention generally relates to the field of biomedical data analysis. In particular, the present invention is directed to apparatus and methods for identification of abnormal biomedical features from images of biomedical data.

BACKGROUND

Early detection of medically relevant features in biomedical data plays a crucial role in the timely diagnosis and treatment of many challenging medical conditions such as atrial fibrillation. However, medical professionals are often faced with a large quantity of unlabeled clinical data that potentially obscure the detection of these medically relevant features. In addition, biomedical data such as electrocardiogram (ECG) data are often recorded or stored in a physical format, such as on paper, and analyzing such biomedical data typically requires a manual analysis by a specialist.

SUMMARY OF THE DISCLOSURE

In an aspect, an apparatus for identification of abnormal biomedical features within images of biomedical data is described. Apparatus includes an image capture device, a processor communicatively connected to the image capture device, a memory communicatively connected to the processor, and a display device communicatively connected to the processor, wherein the image capture device is configured to capture at least an image of biomedical data pertaining to a first patient, the memory contains instructions configuring the processor to receive the image of biomedical data from the image capture device, extract a plurality of biomedical features as a function of the biomedical data, receive repository data from a medical repository as a function of the plurality of biomedical features, generate at least a distance metric as a function of the plurality of biomedical features and the repository data, and highlight at least a biomedical feature within the image as a function of the at least a distance metric, and the display device is configured to display the at least a highlighted biomedical feature within the image.

In another aspect, a method for identification of abnormal biomedical features within images of biomedical data is described. Method includes capturing, using an image capture device, at least an image of biomedical data pertaining to a first patient, receiving, by a processor from the image capture device, the image of biomedical data, extracting, by the processor, a plurality of biomedical features as a function of the biomedical data, receiving, by the processor, repository data from a medical repository as a function of the plurality of biomedical features, generating, by the processor, at least a distance metric as a function of the plurality of biomedical features and the repository data, highlighting, by the processor, at least a biomedical feature within the image as a function of the at least a distance metric, and displaying, using a display device, the at least a highlighted biomedical feature within the image.

These and other aspects and features of non-limiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for identification of abnormal biomedical features within images of biomedical data. Apparatus includes an image capture device, a processor communicatively connected to the image capture device, a memory communicatively connected to the processor, and a display device communicatively connected to the processor. In one or more embodiments, image capture device may be configured to capture at least an image of biomedical data pertaining to a first patient; the processor may be configured to receive the at least an image, extract a plurality of biomedical features as a function of the biomedical data therein, receive repository data from a medical repository as a function of the plurality of biomedical features, generate at least a distance metric as a function of the plurality of biomedical features and the repository data, highlight at least a biomedical feature within the at least an image as a function of the at least a distance metric; and the display device is configured to display within a user interface the at least a highlighted biomedical feature within the at least an image, as a color-coded heat map.

Aspects of the present disclosure may be used to provide efficient clinical decision support for medical professionals by promptly identifying one or more abnormal features within an image of biomedical data. Aspects of the present disclosure may allow for fast suggestion of medical conditions without time-consuming manual analysis by a specialist. Aspects of the present disclosure may provide possibilities in gleaning useful information from a large quantity of data collected from a population over an extended period of time. Exemplary embodiments illustrating aspects of the present disclosure are described below in the context of several specific examples.

Figure 1:
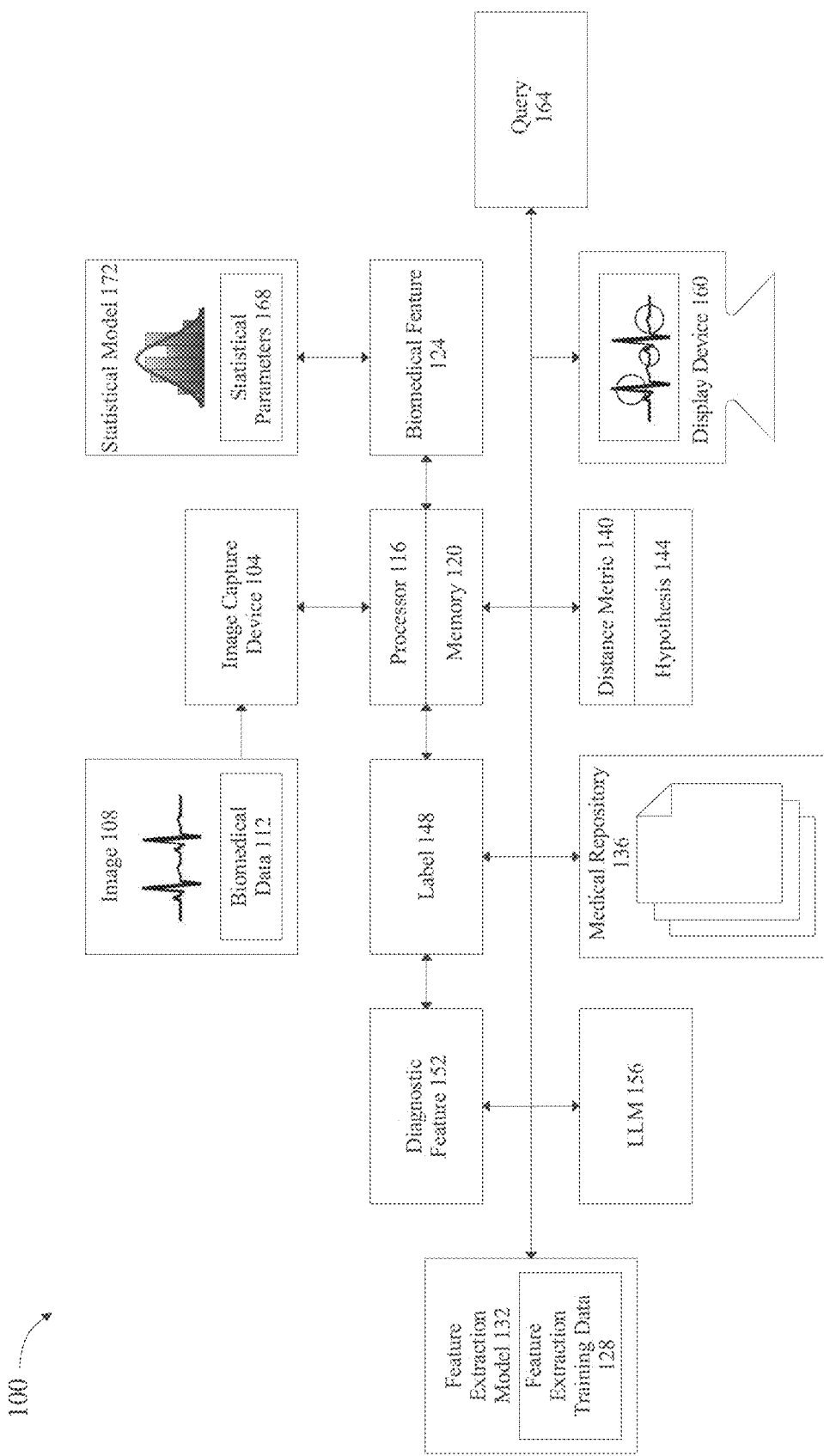
FIG. 1 is an exemplary embodiment of an apparatus that identifies abnormal biomedical features within images of biomedical data.

Referring now to FIG. 1, an apparatus 100 for identifying abnormal biomedical features within images 108 of biomedical data 112 is illustrated. Apparatus 100 comprises an image capture device 104, wherein the image capture device 104 is configured to capture at least an image 108 of biomedical data 112 pertaining to a first patient. In some embodiments, image 108 may include a CT scan, echocardiogram, X-ray, electrocardiogram, or any other medical imaging modality. For the purposes of this disclosure, an "image capture device" is a device capable of recording a digital representation of an object. Image capture device 104 may include any type of image capture device accessible to a person of ordinary skill in the art, and/or deemed suitable by a person of ordinary skill in the art upon reviewing the entirety of this disclosure. In one or more embodiments, image capture device 104 may include a camera. For the purposes of this disclosure, a "camera" is a single device or an assembly of multiple devices configured to detect at least one type of electromagnetic radiation and generate a graphical representation therefrom. As nonlimiting examples, camera may detect visible light, infrared light, ultraviolet light, or X-ray. In one or more embodiments, camera may include one or more optics; nonlimiting examples of optics include spherical lenses, aspherical lenses, reflectors, polarizers, filters, windows, aperture stops, and the like. In one or more embodiments, camera may include an image sensor. Exemplary image sensors include digital image sensors, such as without limitation charge-coupled device (CCD) sensors and complimentary metal-oxide-semiconductor (CMOS) sensors. As a nonlimiting example, camera may include a remote camera device communicatively connected to a computing device, such as a portable camera connected to a desktop or laptop computer through either a cord or wireless connection. As a nonlimiting example, camera may include a camera integrated within a computing device, such as a built-in camera of a laptop computer. As another nonlimiting example, camera may include a camera integrated within a remote and/or portable device, such as a built-in camera of a smartphone or a tablet. For the purposes of this disclosure, an "image" is a visual representation of data. In some embodiments, image may be product of image capture device 104. In some embodiments, image may contain digital information representing at least a physical scene, space, and/or object. In one or more embodiments, image 108 may be an optical image, such as without limitation an image of an object generated by at least an optic. In some cases, image 108 may be a digital representation of another image, such as a digital image of a printed photograph or the like captured using a built-in camera of a smartphone. Alternatively, image 108 may comprise a plurality of images 108 arranged in sequence as a function of time, such as one or more videos. In some embodiments, image 108 may include a digital image. Digital image may be in a format such as jpeg, png, pdf, btmp, and the like. In some embodiments digital image may be retrieved from an electronic health record.

With continued reference to FIG. 1, for the purposes of this disclosure, a "patient" is a human or any individual organism, on whom or on which a procedure, study, or otherwise experiment, may be conducted. As nonlimiting examples, patient may include human patient with symptoms of atrial fibrillation, an individual undergoing cardiac screening, a participant in a clinical trial, an individual with congenital heart disease, a heart transplant candidate, an individual receiving follow-up care after cardiac surgery, a healthy volunteer, an individual with heart failure, or the like. Additionally or alternatively, patient may include an animal model (i.e., an animal used to model certain medical conditions such as a laboratory rat).

With continued reference to FIG. 1, for the purposes of this disclosure, "biomedical data" are data describing one or more biological, physiological, or biomedical features or functions of patient; they may include any relevant form or type of data of which an image or photograph may be captured. In one or more embodiments, biomedical data 112 may include medical data collected by a medical professional and/or results generated therefrom, such as without limitation pathology test results, X-ray data, echocardiogram (ECG), electroencephalogram (EEG), magnetic resonance imaging (MRI) data, computed tomography (CT) data, ultrasound imaging data including intracardiac echocardiogram (ICE), transthoracic echocardiogram frame, and/or transesophageal echocardiogram (TEE) data, optical images, digital photographs, and/or the like. For the purposes of this disclosure, an "electrocardiogram (ECG)" is a recording of electrical activity of patient's heart over a period of time; "ECG" and "ECG data" may be used interchangeably throughout this disclosure. In one or more embodiments, ECG data may include one or more recordings captured by a plurality (e.g., 12) of electrodes placed on patient's skin. In one or more embodiments, ECG data may include information regarding a P wave, T wave, QRS complex, PR interval, ST segment, and/or the like, as described in detail below in this disclosure. In one or more embodiments, ECG data may be used to identify specific cardiac events or phases of a cardiac cycle, e.g., isovolumic relaxation, ventricular filling, isovolumic contraction, and rapid ventricular ejection. As a nonlimiting example, ECG described herein may be consistent with any ECG data disclosed in U.S. patent application Ser. No. 18/229,854, filed on Aug. 3, 2023, entitled "APPARATUS AND METHOD FOR DETERMINING A PATIENT SURVIVAL PROFILE USING ARTIFICIAL INTELLIGENCE-ENABLED ELECTROCARDIOGRAM (ECG)", the entirety of which is incorporated herein by reference. For the purposes of this disclosure, an "electroencephalogram (EEG)" is an electrogram of the spontaneous electrical activity of the brain measured using small, metal discs (electrodes) attached to the scalp; it provides useful diagnostic information related to brain disorders.

With continued reference to FIG. 1, for the purposes of this disclosure, computed tomography (CT) is a medical imaging technique that uses X-rays to capture cross-sectional images (slices) of a patient's body; by taking a plurality of slices, a CT scan creates a detailed three-dimensional (3D) representation of internal structures. For the purposes of this disclosure, an "ICE frame" is a 2D ultrasound image that represents anatomy (i.e., walls, chambers, blood vessels, etc.) of at least part of a heart, as described above. For the purposes of this disclosure, a "transthoracic echocardiogram (TTE) frame" is a two-dimensional (2D) ultrasound image collected by placing a probe or ultrasound transducer on patient's chest or abdomen to collect various views of heart. For the purposes of this disclosure, a "transesophageal echocardiogram (TEE) frame" is a 2D ultrasound image collected by passing a specialized probe containing an ultrasound transducer at its tip into patient's esophagus; it is an alternative way of performing echocardiography. For the purposes of this disclosure, "echocardiography" is an imaging technique that uses ultrasound to examine a heart, the resulting visual image of which is an echocardiogram.

With continued reference to FIG. 1, in one or more embodiments, biomedical data 112 may include time series data of patient. For the purposes of this disclosure, "time series data" are data measured as a function of time and/or recorded over consistent intervals of time. In one or more embodiments, time series data may include information related to patient's health and recorded over weeks, months, years, or decades. For example, and without limitation, time series data may include parameters such as weight, body fat, bone density, blood pressure, cholesterol levels, tobacco/alcohol consumption, substance usage, prescription dosage, or the like. In one or more embodiments, time series data may include one or more signals or parameters, such as voltage in ECG or EEG, measured using one or more medical facilities over a short time span.

With continued reference to FIG. 1, biomedical data 112 may be associated with one or more electronic health records (EHR) of patient. For the purposes of this disclosure, an electronic health record (EHR) is a comprehensive collection of records relating to the health history, diagnosis, or condition of patient, relating to treatment provided or proposed to be provided to the patient, or relating to additional factors that may impact the health of the patient; elements within an EHR, once combined, may provide a detailed picture of patient's overall health. In one or more embodiments, biomedical data 112 may be deposited to and retrieved from one or more EHRs in order to capture image 108. In one or more embodiments, EHR may include demographic data of patient; for example, and without limitation, EHR may include basic information about patient such as name, age, gender, ethnicity, socioeconomic status, and/or the like. In one or more embodiments, each EHR may also include patient's medical history; for example, and without limitation, EHR may include a detailed record of patient's past health conditions, medical procedures, hospitalizations, and illnesses such as surgeries, treatments, medications, allergies, and/or the like. In one or more embodiments, each EHR may include lifestyle information of patient; for example, and without limitation, EHR may include details about the patient's diet, exercise habits, smoking and alcohol consumption, and other behaviors that could impact patient's health. In one or more embodiments, EHR may include patient's family history; for example, and without limitation, EHR may include a record of hereditary diseases. In one or more embodiments, a database may comprise a plurality of EHRs. In one or more embodiments, EHRs may be retrieved from a repository of similar nature as database. Details regarding databases will be provided below in this disclosure.

With continued reference to FIG. 1, apparatus 100 comprises a processor 116 communicatively connected to image capture device 104. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low-power wide-area network, optical communication, magnetic, capacitive, or optical coupling, and the like. In some instances, the terminology "communicatively coupled" may be used in place of communicatively connected in this disclosure.

With continued reference to FIG. 1, in one or more embodiments, processor 116 may include a computing device. Computing device could include any analog or digital control circuit, including an operational amplifier circuit, a combinational logic circuit, a sequential logic circuit, an application-specific integrated circuit (ASIC), a field programmable gate arrays (FPGA), or the like. Computing device may include a processor communicatively connected to a memory, as described above. Computing device may include any computing device as described in this disclosure, including without limitation a microcontroller, microprocessor, digital signal processor, and/or system on a chip as described in this disclosure. Computing device may include, be included in, and/or communicate with a mobile device such as a mobile telephone, smartphone, or tablet. Computing device may include a single computing device operating independently, or may include two or more computing device operating in concert, in parallel, sequentially, or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a first computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a nonlimiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1, apparatus 100 includes a memory 120 communicatively connected to processor 116, wherein the memory 120 contains instructions configuring the processor 116 to perform any processing steps described herein.

With continued reference to FIG. 1, computing device may perform determinations, classification, and/or analysis steps, methods, processes, or the like as described in this disclosure using machine learning processes. For the purposes of this disclosure, a "machine learning process" is a process that automatedly uses a body of data known as "training data" and/or a "training set" to generate an algorithm that will be performed by a processor module to produce outputs given data provided as inputs; this is in contrast to a nonmachine learning software program where the commands to be executed are determined in advance by a user and written in a programming language. A machine learning process may utilize supervised, unsupervised, lazy-learning processes and/or neural networks. More details regarding computing devices and machine learning processes will be provided below.

With continued reference to FIG. 1, in one or more embodiments, one or more machine learning models may be used to perform certain function or functions of apparatus 100, such as extraction of a plurality of biomedical features, as described below. Processor 116 may use a machine learning module to implement one or more algorithms as described herein or generate one or more machine learning models, such as feature extraction model, as described below. However, machine learning module is exemplary and may not be necessary to generate one or more machine learning models and perform any machine learning described herein. In one or more embodiments, one or more machine learning models may be generated using training data. Training data may include inputs and corresponding predetermined outputs so that machine learning model may use correlations between the provided exemplary inputs and outputs to develop an algorithm and/or relationship that then allows the machine learning model to determine its own outputs for inputs. Training data may contain correlations that a machine learning process may use to model relationships between two or more categories of data elements. Exemplary inputs and outputs may be retrieved from a database, selected from one or more EHRs, or be provided by a user. In one or more embodiments, machine learning module may obtain training data by querying a communicatively connected database that includes past inputs and outputs. Training data may include inputs from various types of databases, resources, and/or user inputs and outputs correlated to each of those inputs, so that machine learning model may determine an output. Correlations may indicate causative and/or predictive links between data, which may be modeled as relationships, such as mathematical relationships, by machine learning models, as described in further detail below. In one or more embodiments, training data may be formatted and/or organized by categories of data elements by, for example, associating data elements with one or more descriptors corresponding to categories of data elements. As a nonlimiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In one or more embodiments, training data may include previous outputs such that one or more machine learning models may iteratively produce outputs.

With continued reference to FIG. 1, in one or more embodiments, processor 116 may implement one or more aspects of "generative artificial intelligence (AI)", a type of AI that uses machine learning algorithms to create, establish, or otherwise generate data such as, without limitation, interpretations of medical data. In one or more embodiments, machine learning module described below in this disclosure may generate one or more generative machine learning models that are trained on one or more prior iterations. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

With continued reference to FIG. 1, processor 116 is configured to receive the image 108 of biomedical data 112 from image capture device 104. In one or more embodiments, processor 116 and/or computing device may transform image 108 to a high-quality image and build subsequent downstream tasks using this high-quality image. In one or more embodiments, receiving image 108 of biomedical data 112 may comprise transforming the image into an in-silicon image, wherein processor 116 is configured to extract a plurality of biomedical parameters from image 108 of biomedical data 112, convert the plurality of biomedical parameters to one or more digitized signals, and transform the one or more digitized signals into the in-silicon image. For the purposes of this disclosure, a "signal" is any intelligible representation of data, for example from one device to another. A signal may include an optical signal, a hydraulic signal, a pneumatic signal, a mechanical signal, an electric signal, a digital signal, an analog signal, and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 132 [printer port]), and the like. For the purposes of this disclosure, an "in-silicon image" is a computer-generated, abstract representation of a real image after eliminating noises, defects, aberrations, backgrounds, and the like. In some cases, image 108 containing time-dependent biomedical data 112 may be converted and simplified to time series data (i.e., f(t) as a function of t), as described above. In some cases, transforming image 108 into an in-silicon image may comprise transforming the image into an in-silicon image using a transformer model. Downstream models may be trained using these transformed images, which eliminates the need for having images of different qualities in the dataset for different downstream tasks.

With continued reference to FIG. 1, additionally and/or alternatively, in one or more embodiments, receiving image 108 of biomedical data 112 may comprise comparing the biomedical data 112 against at least a quality assurance parameter. In one or more embodiments, receiving image 108 of biomedical data 112 may comprise validating one or more digitized signals by classifying the one or more digitized signals to a plurality of preliminary parameters and determining an accuracy status of plurality of biomedical parameters by comparing the plurality of preliminary parameters to the plurality of biomedical parameters, and generating a quality diagnostic of the biomedical data based on the result of the validation. As a nonlimiting example, one or more parameters may be calculated from biomedical data 112 within the image 108 and compared/calibrated to one or more parameters extracted from textual components of a reference literature using optical character recognition (OCR, as described below). Conversion of image 108 into time series data, generation of an image from such time series data, and/or quality assurance related thereto may be performed consistently with details disclosed in U.S. patent application Ser. No. 18/591,499, filed on Feb. 29, 2024, and entitled "APPARATUS AND METHOD FOR TIME SERIES DATA FORMAT CONVERSION AND ANALYSIS", U.S. patent application Ser. No. 18/599,435, filed on Mar. 8, 2024, and entitled "AN APPARATUS AND METHOD FOR GENERATING A QUALITY DIAGNOSTIC OF ECG (ELECTROCARDIOGRAM) DATA", U.S. patent application Ser. No. 18/641,217, filed on Apr. 19, 2024, and entitled "SYSTEMS AND METHODS FOR TRANSFORMING ELECTROCARDIOGRAM IMAGES FOR USE IN ONE OR MORE MACHINE LEARNING MODELS", and U.S. patent application Ser. No. 18/652,364, filed on May 1, 2024, and entitled "APPARATUS AND METHOD FOR TRAINING A MACHINE LEARNING MODEL TO AUGMENT SIGNAL DATA AND IMAGE DATA", the entirety of each of which is incorporated herein by reference.

With continued reference to FIG. 1, in one or more embodiments, processor 116 may perform one or more functions of apparatus 100 by using optical character recognition (OCR) to read digital files and extract information therein. In one or more embodiments, OCR may include automatic conversion of images (e.g., typed, handwritten, or printed text) into machine-encoded text. In one or more embodiments, recognition of at least a keyword from an image component may include one or more processes, including without limitation OCR, optical word recognition, intelligent character recognition, intelligent word recognition, and the like. In one or more embodiments, OCR may recognize written text one glyph or character at a time, for example, for languages that use a space as a word divider. In one or more embodiments, intelligent character recognition (ICR) may recognize written text one glyph or character at a time, for instance by employing machine learning processes. In one or more embodiments, intelligent word recognition (IWR) may recognize written text, one word at a time, for instance by employing machine learning processes.

With continued reference to FIG. 1, in one or more embodiments, OCR may employ preprocessing of image components. Preprocessing process may include without limitation de-skew, de-speckle, binarization, line removal, layout analysis or "zoning", line and word detection, script recognition, character isolation or "segmentation", and normalization. In one or more embodiments, a de-skew process may include applying a transform (e.g., homography or affine transform) to an image component to align text. In one or more embodiments, a de-speckle process may include removing positive and negative spots and/or smoothing edges. In one or more embodiments, a binarization process may include converting an image from color or greyscale to black-and-white (i.e., a binary image). Binarization may be performed as a simple way of separating text (or any other desired image component) from the background of image component. In one or more embodiments, binarization may be required for example if an employed OCR algorithm only works on binary images. In one or more embodiments, line removal process may include removal of non-glyph or non-character imagery (e.g., boxes and lines). In one or more embodiments, a layout analysis or "zoning" process may identify columns, paragraphs, captions, and the like as distinct blocks. In one or more embodiments, a line and word detection process may establish a baseline for word and character shapes and separate words, if necessary. In one or more embodiments, a script recognition process may, for example in multilingual documents, identify a script, allowing an appropriate OCR algorithm to be selected. In one or more embodiments, a character isolation or "segmentation" process may separate signal characters, for example, character-based OCR algorithms. In one or more embodiments, a normalization process may normalize the aspect ratio and/or scale of image component.

With continued reference to FIG. 1, in one or more embodiments, an OCR process may include an OCR algorithm. Exemplary OCR algorithms include matrix-matching processes and/or feature extraction processes. Matrix matching may involve comparing an image to a stored glyph on a pixel-by-pixel basis. In one or more embodiments, matrix matching may also be known as "pattern matching", "pattern recognition", and/or "image correlation". Matrix matching may rely on an input glyph being correctly isolated from the rest of image component. Matrix matching may also rely on a stored glyph being in a similar font and at the same scale as input glyph.

With continued reference to FIG. 1, in one or more embodiments, an OCR process may include a feature extraction process. In one or more embodiments, feature extraction may decompose a glyph into features. Exemplary nonlimiting features may include corners, edges, lines, closed loops, line direction, line intersections, and the like. In one or more embodiments, feature extraction may reduce the dimensionality of representation and may make the recognition process computationally more efficient. In one or more embodiments, extracted features can be compared with an abstract vector-like representation of a character, which might be reduced to one or more glyph prototypes. General techniques of feature detection in computer vision are applicable to this type of OCR. In one or more embodiments, machine learning process like nearest neighbor classifiers (e.g., k-nearest neighbors algorithm) can be used to compare image features with stored glyph features and choose a nearest match. OCR may employ any machine learning process described in this disclosure. Exemplary nonlimiting OCR software includes Cuneiform and Tesseract. Cuneiform is a multi-language, open-source OCR system originally developed by Cognitive Technologies of Moscow, Russia. Tesseract is a free OCR software originally developed by Hewlett-Packard of Palo Alto, California, United States.

With continued reference to FIG. 1, in one or more embodiments, OCR may employ a two-pass approach to character recognition. Second pass may include adaptive recognition and use letter shapes recognized with high confidence on a first pass to better recognize remaining letters on a second pass. In one or more embodiments, two-pass approach may be advantageous for unusual fonts or low-quality image components where visual verbal content may be distorted. Another exemplary OCR software tool includes OCRopus. The development of OCRopus is led by the German Research Center for Artificial Intelligence in Kaiserslautern, Germany. In one or more embodiments, OCR software may employ neural networks, for example, deep neural networks, as described in this disclosure below.

With continued reference to FIG. 1, in one or more embodiments, OCR may include post-processing. For example, OCR accuracy can be increased, in some cases, if output is constrained by a lexicon. A lexicon may include a list or set of words that are allowed to occur in a document. In one or more embodiments, a lexicon may include, for instance, all the words in the English language, or a more technical lexicon for a specific field. In some cases, an output stream may be a plain text stream or file of characters. In one or more embodiments, an OCR may preserve an original layout of visual verbal content. In one or more embodiments, near-neighbor analysis can make use of co-occurrence frequencies to correct errors by noting that certain words are often seen together. For example, "Washington, D.C." is generally far more common in English than "Washington DOC". In one or more embodiments, an OCR process may make use of a priori knowledge of grammar for a language being recognized. For example, OCR process may apply grammatical rules to help determine if a word is likely to be a verb or a noun. Distance conceptualization may be employed for recognition and classification. For example, a Levenshtein distance algorithm may be used in OCR post-processing to further optimize results. A person of ordinary skill in the art will recognize how to apply the aforementioned technologies to extract information from a digital file upon reviewing the entirety of this disclosure.

With continued reference to FIG. 1, in one or more embodiments, a computer vision module configured to perform one or more computer vision tasks such as, without limitation, object recognition, feature detection, edge/corner detection thresholding, or machine learning process may be used to recognize specific features or attributes. For the purposes of this disclosure, a "computer vision module" is a computational component designed to perform one or more computer vision, image processing, and/or modeling tasks. In one or more embodiments, computer vision module may receive one or more digital files containing one or more reference attributes from a data repository and generate one or more labels as a function of the received one or more reference attributes. In one or more embodiments, to generate a plurality of labels, computer vision module may be configured to compare one or more reference attributes against the statistical data of the one or more reference attributes and attach one or more labels as a function of the comparison, as described below.

With continued reference to FIG. 1, in one or more embodiments, computer vision module may include an image processing module, wherein images may be pre-processed using the image processing module. For the purposes of this disclosure, an "image processing module" is a component designed to process digital images such as images described herein. For example, and without limitation, image processing module may be configured to compile a plurality of images of a multi-layer scan to create an integrated image. In one or more embodiments, image processing module may include a plurality of software algorithms that can analyze, manipulate, or otherwise enhance an image, such as, without limitation, a plurality of image processing techniques as described below. In one or more embodiments, computer vision module may also include hardware components such as, without limitation, one or more graphics processing units (GPUs) that can accelerate the processing of a large number of images. In one or more embodiments, computer vision module may be implemented with one or more image processing libraries such as, without limitation, OpenCV, PIL/Pillow, ImageMagick, and the like. In a nonlimiting example, in order to generate one or more labels and/or recognize one or more reference attributes, one or more image processing tasks, such as noise reduction, contrast enhancement, intensity normalization, image segmentation, and/or the like, may be performed by computer vision module on a plurality of images to isolate certain features or components from the rest. In one or more embodiments, one or more machine learning models may be used to perform segmentations, for example, and without limitation, a U-net (i.e., a convolution neural network containing a contracting path as an encoder and an expansive path as a decoder, wherein the encoder and the decoder forms a U-shaped structure). A person of ordinary skill in the art, upon reviewing the entirety of this disclosure, will be aware of various image processing, computer vision, and modeling tasks that may be performed by processor 116.

With continued reference to FIG. 1, in one or more embodiments, one or more functions of apparatus 100 may involve a use of image classifiers to classify images within any data described in this disclosure. For the purposes of this disclosure, an "image classifier" is a machine learning model, such as a mathematical model, neural net, or program generated by a machine learning algorithm known as a "classification algorithm", as described in further detail below, that sort inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device and/or another device may generate image classifier using a classification algorithm. For the purposes of this disclosure, a classification algorithm is a process whereby computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, processor 116 may use image classifier to identify a key image in any data described in this disclosure. For the purposes of this disclosure, a "key image" is an element of visual data used to identify and/or match elements to each other. In one or more embodiments, key image may include part of a medical image such as a CT scan, an MRI scan, or the like, with features that unambiguously identify the type of the medical image. Image classifier may be trained with binarized visual data that have already been classified to determine key images in any other data described in this disclosure. For the purposes of this disclosure, "binarized visual data" are visual data that are described in a binary format. For example, binarized visual data of a photo may comprise ones and zeroes, wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g., image 108) described in this disclosure and output a key image with the data. In one or more embodiments, image classifier may be used to compare visual data in one data set, such as image 108, with visual data in another data set, such as one or more images within a medical repository, as described below.

With continued reference to FIG. 1, processor 116 may be configured to perform feature extraction on image 108 and/or one or more images within medical repository, as described below. For the purposes of this disclosure, "feature extraction" is a process of transforming an initial data set into informative measures and values. For example, feature extraction may include a process of determining one or more geometric features of an anatomic structure. In one or more embodiments, feature extraction may be used to determine one or more spatial relationships within a drawing that may be used to uniquely identify one or more features. In one or more embodiments, processor 116 may be configured to extract one or more regions of interest, wherein the regions of interest may be used to extract one or more features using one or more feature extraction techniques.

With continued reference to FIG. 1, processor 116 may be configured to perform one or more of its functions, such as extraction of biomedical features, as described below, using a feature learning algorithm. For the purposes of this disclosure, a "feature learning algorithm" is a machine learning algorithm that identifies associations between elements of data in a data set, which may include without limitation a training data set, where particular outputs and/or inputs are not specified. For instance, and without limitation, a feature learning algorithm may detect co-occurrences of elements of data, as defined above, with each other. Computing device may perform feature learning algorithm by dividing elements or sets of data into various sub-combinations of such data to create new elements of data and evaluate which elements of data tend to co-occur with which other elements. In one or more embodiments, feature learning algorithm may perform clustering of data.

With continued reference to FIG. 1, feature learning and/or clustering algorithm may be implemented, as a non-limiting example, using a k-means clustering algorithm. For the purposes of this disclosure, a "k-means clustering algorithm" is a type of cluster analysis that partitions n observations or unclassified cluster data entries into k clusters in which each observation or unclassified cluster data entry belongs to the cluster with the nearest mean. For the purposes of this disclosure, "cluster analysis" is a process that includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering, whereby each observation or unclassified cluster data entry belongs to a cluster or not. Cluster analysis may include soft clustering or fuzzy clustering, whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa, as described below. Cluster analysis may include strict partitioning clustering, whereby each observation or unclassified cluster data entry belongs to exactly one cluster. Cluster analysis may include strict partitioning clustering with outliers, whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering, whereby observations or unclassified cluster data entries that belong to a child cluster also belong to a parent cluster.

With continued reference to FIG. 1, computing device may generate a k-means clustering algorithm by receiving unclassified data and outputting a definite number of classified data entry clusters, wherein the data entry clusters each contain cluster data entries. K-means algorithm may select a specific number of groups or clusters to output, identified by a variable "k". Generating k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, which may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids ci of centroids in set C. Unclassified data may be assigned to a cluster based on $\mathrm{argmin}_{c_i \ni C}$ dist(ci, x)$^2$, where ar gmin includes argument of the minimum, ci includes a collection of centroids in a set C, and dist includes standard Euclidean distance. K-means clustering module may then recompute centroids by taking a mean of all cluster data entries assigned to a centroid's cluster. This may be calculated based on $c_i = 1/|S_i| \Sigma x_i \ni S_i^{x_i}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering algorithm may be configured to calculate a degree of similarity index value. For the purposes of this disclosure, a "degree of similarity index value" is a distance measured between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between the element to be compared and/or clustered and a particular cluster.

With continued reference to FIG. 1, k-means clustering algorithm selects a classified data entry cluster as a function of the degree of similarity index value. In one or more embodiments, k-means clustering algorithm may select a classified data entry cluster with the smallest degree of similarity index value indicating a high degree of similarity between an element and the data entry cluster. Alternatively or additionally, k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; a person of ordinary skills in the art, upon reviewing the entirety of this disclosure, will be aware of various additional or alternative feature learning approaches, such as particle swarm optimization (PSO) and generative adversarial network (GAN) that may be used consistently with this disclosure.

With continued reference to FIG. 1, in one or more embodiments, processor 116 may use an image recognition algorithm to determine patterns within an image. In one or more embodiments, image recognition algorithm may include an edge-detection algorithm, which may detect one or more shapes defined by edges. For the purposes of this disclosure, an "edge detection algorithm" is or includes a mathematical method that identifies points in a digital image at which the image brightness changes sharply and/or has discontinuities. In one or more embodiments, such points may be organized into straight and/or curved line segments, which may be referred to as "edges". Edge detection may be performed using any suitable edge detection algorithm, including without limitation Canny edge detection, Sobel operator edge detection, Prewitt operator edge detection, Laplacian operator edge detection, and/or differential edge detection. Edge detection may include phase congruency-based edge detection, which finds all locations of an image where all sinusoids in the frequency domain, for instance when generated using a Fourier decomposition, may have matching phases which may indicate a location of an edge.

With continued reference to FIG. 1, processor 116 is configured to extract a plurality of biomedical features 124 as a function of biomedical data 112. Extraction of plurality of biomedical features 124 may be consistent with any type of feature extraction process described in this disclosure or otherwise incorporated herein by reference. As a nonlimiting example, when biomedical data 112 includes at least an ECG, at least a biomedical feature 124 may include at least an ECG feature identified from the at least an ECG, as described above. As another nonlimiting example, when biomedical data 112 includes time series data, at least a biomedical feature 124 may include at least a feature identified from the time series data, as described above. In one or more embodiments, extracting plurality of biomedical features 124 may comprise receiving feature extraction training data 128 comprising a plurality of training images as inputs and a plurality of training biomedical features as outputs, training a feature extraction model 132 by correlating the plurality of training images with the plurality of training biomedical features, and extracting the plurality of biomedical features 124 from the image 108 using the trained feature extraction model 132. Implementation of this machine learning model may be consistent with any type of machine learning model or algorithm described in this disclosure. In one or more embodiments, feature extraction training data may include data specifically synthesized for training purposes using one or more generative models, as described in this disclosure. As a nonlimiting example, training data may be extracted from medical literature. In one or more embodiments, one or more historic queries may be incorporated into feature extraction training data upon validation. In one or more embodiments, feature extraction training data 128 may be retrieved from one or more databases, EHRs, and/or other repositories of similar nature, or be supplied as one or more user inputs. In one or more embodiments, at least a portion of feature extraction training data may be added, deleted, replaced, or otherwise updated as a function of one or more inputs from one or more users.

With continued reference to FIG. 1, processor 116 is configured to receive repository data from a medical repository 136 as a function of plurality of biomedical features 124. For the purposes of this disclosure, a "medical repository" is a structured collection of biomedical data to which another set of biomedical data may be compared in order to obtain one or more results and/or initiate one or more steps. In some embodiments, medical repository may include a database. In some embodiments, medical repository may include electronic health record (EHR) data. For the purposes of this disclosure, repository data are biomedical data within medical repository 136 that serve as a reference, to which biomedical features 124 may be compared. In one or more embodiments, receiving repository data may comprise applying one or more inclusion/exclusion criteria to the repository data to select a subset thereof. As a nonlimiting example, processor 116 may identify demographic information of first patient within image 108, as described above, and isolate within medical repository 136 a cohort of patients from the same age group, of the same gender, and/or of the same overall health. Additional details will be provided below in this disclosure. In some cases, medical repository 136 may include data, such as without limitation, clinical data, research findings, case studies, diagnostic criteria, treatment outcomes, patient records, and/or the like. In one or more embodiments, medical repository 136 may include or be linked to one or more EHRs, as described above. Additionally and/or alternatively, medical repository 136 may include or be linked to a centralized or distributed source of medical data such as a hospital information system (HIS), regional health information organization (RHIO), health information exchange (HIE), cloud-based EHR platform, research database and biobank, public health database, clinical registry, among others. Medical repository 136 may include one or more databases or the like and may be implemented in any manner suitable for implementation of databases. Database may be implemented, without limitation, as a relational database, a key-value retrieval database such as a NoSQL database, or any other format or structure for use as database that a person of ordinary skill in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described in this disclosure. Data entries in database may be flagged with or linked to one or more additional elements of information, which may be reflected in data entry cells and/or in linked tables such as tables related by one or more indices in database or another relational database. A person of ordinary skill in the art, upon reviewing the entirety of this disclosure, will be aware of various ways in which data entries in database may store, retrieve, organize, and/or reflect data and/or records as used herein, as well as categories and/or populations of data consistently with this disclosure.

With continued reference to FIG. 1, processor 116 is configured to generate at least a distance metric 140 as a function of the plurality of biomedical features 124 and repository data. For the purposes of this disclosure, a "distance metric" is a type of metric used in machine learning to calculate similarity between data. Common types of distance metrics may include Euclidean Distance, Manhattan Distance, Minkowski Distance, and Hamming Distance. As a nonlimiting example, a small distance metric 140 between biomedical feature 124 and a reference feature associated with a healthy patient may indicate a normal biomedical feature 124, whereas a large distance metric 140 between biomedical feature 124 and a reference feature associated with a healthy patient may indicate an abnormal biomedical feature 124. In some cases, generating at least a distance metric 140 may include selecting one or more cutoffs, such as without limitation an absolute numerical value or a percentage, that may be used to categorize the at least a distance metric 140 into one or more categories. As a nonlimiting example, a biomedical feature 124 may be classified as an outlier if its associated distance metric 140 exceeds two standard deviations compared to the statistical average of repository data, as described below. A person of ordinary skill in the art, upon reviewing the entirety of this disclosure, will be able to identify suitable means to implement distance metric 140 for apparatus 100. Alternatively and/or additionally, in one or more embodiments, processor 116 may be configured to generate at least a hypothesis 144 as a function of at least a biomedical feature 124 of plurality of biomedical features 124. In one or more embodiments, generation of at least a hypothesis 144 may involve generation of the at least a hypothesis 144 using a generative model.

With continued reference to FIG. 1, processor 116 may be configured to generate at least a distance metric 140 and/or a plurality of hypotheses 144 by creating a plurality of labels 148, wherein each label 148 of the plurality of labels 148 represents a diagnostic feature 152 associated with one or more hypotheses 144 within the plurality of hypotheses 144, and identify at least a hypothesis 144 from the plurality of hypotheses 144 by matching at least a biomedical feature 124 of the plurality of biomedical features 124 against at least a label 148 of the plurality of labels 148. In some cases, identifying at least a hypothesis 144 may comprise ranking plurality of hypotheses 144 as a function of a set of predetermined criteria; and identifying the least a hypothesis 144 from the plurality of hypotheses 144 as a function of the rank of the plurality of hypotheses. For the purposes of this disclosure, "labeling" is a process of identifying raw data (images, text files, videos, etc.) and adding one or more meaningful and informative labels 148 to provide a context for one or more following steps. For the purposes of this disclosure, a "label" is an indication describing one or more characteristics of a subject matter (e.g., one or more diagnostic features 144) as well as how the subject matter may be categorized into one or more categories with respect to a population or sub-population containing the subject. In one or more embodiments, label 148 may include a binary label, e.g., "normal" vs. "abnormal" or "included" vs. "not included". In one or more embodiments, label 148 may be further specified, such as "abnormally large", "abnormally small", "abnormally high", or "abnormally low". In one or more embodiments, label 148 may be associated with a percentile ranking, e.g., "top 10% of the population". In one or more embodiments, label 148 may be applied with respect to at least a specific cohort upon application of one or more inclusion/exclusion criteria, such as "top 25% of the female population". In some cases, labeling one or more diagnostic feature 144 as a function of one or more hypotheses 144 may comprise analyzing the statistical distribution of plurality of diagnostic features 144, as described below.

With continued reference to FIG. 1, in one or more embodiments, identifying at least a hypothesis 144 may comprise validating the at least a hypothesis 144. For the purposes of this disclosure, "validation" is a process of confirming whether hypothesis 144 is correct or not based on an independent information source; it may be either automated or manual. In one or more embodiments, results of validation may be binary, i.e., "correct" vs. "incorrect". In one or more embodiments, results of validation may be expressed on one or more continuous scales. As a nonlimiting example, results of validation may include one or more confidence scores, e.g., a 95/100 or a 5/5. Validation of at least a hypothesis 144 may be consistent with any details disclosed in U.S. patent application Ser. No. 18/648,059, filed on Apr. 26, 2024, and entitled "APPARATUS AND METHODS FOR GENERATING DIAGNOSTIC HYPOTHESES BASED ON BIOMEDICAL SIGNAL DATA", the entirety of which incorporated herein by reference. Nonlimiting examples are also provided below in this disclosure.

With continued reference to FIG. 1, in one or more embodiments, generating plurality of hypotheses 144, as described above, may be implemented by training a large language model (LLM) 156 using a large set of medical literature; in some cases, training LLM 156 using large set of medical literature may comprise first pre-training the LLM 156 on a general set of medical literatures; and fine-tuning the LLM 156 on a special set of medical literature, wherein both the general set of medical literature and the special set of medical literature are subsets of the large set of medical literature. Generation of at least a hypothesis 144 may be consistent with any details disclosed in U.S. patent application Ser. No. 18/648,059, filed on Apr. 26, 2024, and entitled "APPARATUS AND METHODS FOR GENERATING DIAGNOSTIC HYPOTHESES BASED ON BIOMEDICAL SIGNAL DATA", the entirety of which incorporated herein by reference. For the purposes of this disclosure, a "large language model" is a deep learning data structure that can recognize, summarize, translate, predict and/or generate text and other content based on knowledge gained from massive datasets. LLMs may be trained on large sets of data. Training sets may be drawn from diverse sets of data such as, as nonlimiting examples, scientific journal articles, medical report documents, EHRs, entity documents, business documents, inventory documentation, emails, user communications, advertising documents, newspaper articles, and the like. In some embodiments, training sets of an LLM may include information from one or more public or private databases. As a nonlimiting example, training sets may include databases associated with an entity. In some embodiments, training sets may include portions of documents associated with the electronic records correlated to examples of outputs. In one or more embodiments, LLM may include one or more architectures based on capability requirements of the LLM. Exemplary architectures may include, without limitation, Generative Pretrained Transformer (GPT), Bidirectional Encoder Representations from Transformers (BERT), Text-To-Text Transfer Transformer (T5), and the like. Architecture choice may depend on a needed capability such generative, contextual, or other specific capabilities.

With continued reference to FIG. 1, in one or more embodiments, LLM may be generally trained. For the purposes of this disclosure, a "generally trained" LLM is a LLM that is trained on a general training set comprising a variety of subject matters, data sets, and fields. In one or more embodiments, LLM may be initially generally trained. Additionally or alternatively, LLM may be specifically trained. For the purposes of this disclosure, a "specifically trained" LLM is a LLM that is trained on a specific training set, wherein the specific training set includes data including specific correlations for the LLM to learn. As a nonlimiting example, LLM may be generally trained on a general training set, then specifically trained on a specific training set. In one or more embodiments, generally training LLM may be performed using unsupervised machine learning process. In one or more embodiments, specific training of LLM may be performed using supervised machine learning process. As a nonlimiting example, specific training set may include information from a database. As a nonlimiting example, specific training set may include text related to the users such as user specific data for electronic records correlated to examples of outputs. In one or more embodiments, training one or more machine learning models may include setting the parameters of the one or more models (weights and biases) either randomly or using a pretrained model. Generally training one or more machine learning models on a large corpus of text data can provide a starting point for fine-tuning on a specific task. A model such as LLM may learn by adjusting its parameters during the training process to minimize a defined loss function, which measures the difference between predicted outputs and ground truth. Once model has been generally trained, the model may then be specifically trained to fine-tune the pretrained model on task-specific data to adapt it to the target task. Fine-tuning may involve training model with task-specific training data, adjusting the model's weights to optimize performance for the particular task. In some cases, this may include optimizing model's performance by fine-tuning hyperparameters such as learning rate, batch size, and regularization. Hyperparameter tuning may help in achieving the best performance and convergence during training. In one or more embodiments, fine-tuning pretrained model such as LLM may include fine-tuning the pretrained model using Low-Rank Adaptation (LoRA). For the purposes of this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in one or more embodiments, LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. LLM may include a text prediction-based algorithm configured to receive an article and apply a probability distribution to the words already typed in a sentence to work out the most likely word to come next in augmented articles. For example, if some words that have already been typed are "electronic health", then it may be highly likely that the word "record" will come next. LLM may output such predictions by ranking words by likelihood or a prompt parameter. For the example given above, LLM may score "record" as the most likely, "records" as the next most likely, "profile" or "profiles" next, and the like. LLM may include an encoder component and a decoder component.

With continued reference to FIG. 1, LLM may include a transformer architecture. In some embodiments, encoder component of LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. For the purposes of this disclosure, "positional encoding" is a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, LLM and/or transformer architecture may include an attention mechanism. For the purposes of this disclosure, an "attention mechanism" is a part of a neural architecture that enables a system to dynamically quantify relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying attention mechanism, LLM may predict next word by searching for a set of positions in a source sentence where the most relevant information is concentrated. LLM may then predict next word based on context vectors associated with these source positions and all the previously generated target words, such as textual data of a dictionary correlated to a prompt in a training data set. For the purposes of this disclosure, "context vectors" are fixed-length vector representations useful for document retrieval and word sense disambiguation.

With continued reference to FIG. 1, attention mechanism may include, without limitation, generalized attention, self-attention, multi-head attention, additive attention, global attention, and the like. In generalized attention, when a sequence of words or an image is fed to LLM, it may verify each element of input sequence and compare it against the output sequence. Each iteration may involve the mechanism's encoder capturing input sequence and comparing it with each element of the decoder's sequence. From the comparison scores, attention mechanism may then select the words or parts of image that it needs to pay attention to. In self-attention, LLM may pick up particular parts at different positions in input sequence and over time compute an initial composition of output sequence. In multi-head attention, LLM may include a transformer model of an attention mechanism. Attention mechanisms, as described above, may provide context for any position in input sequence. For example, if the input data is a natural-language sentence, the transformer does not have to process one word at a time. In multi-head attention, computations by LLM may be repeated over several iterations, and each computation may form parallel layers known as attention heads. Each separate head may independently pass input sequence and corresponding output sequence element through separate head. A final attention score may be produced by combining attention scores at each head so that every nuance of input sequence is taken into consideration. In additive attention (Bahdanau attention mechanism), LLM may make use of attention alignment scores based on a number of factors. Alignment scores may be calculated at different points in neural network, and/or at different stages represented by discrete neural networks. Source or input sequence words are correlated with target or output sequence words but not to an exact degree. This correlation may take into account all hidden states and the final alignment score is the summation of a matrix of alignment scores. In global attention (Luong mechanism), in situations where neural machine translations are required, LLM may either attend to all source words or predict the target sentence, thereby attending to a smaller subset of words.

With continued reference to FIG. 1, multi-headed attention in encoder may apply a specific attention mechanism called self-attention. Self-attention allows models such as LLM or components thereof to associate each word in input, to other words. As a nonlimiting example, LLM may learn to associate the word "you", with "how" and "are". It's also possible that LLM learns that words structured in this pattern are typically a question and to respond appropriately. In one or more embodiments, to achieve self-attention, input may be fed into three distinct and fully connected neural network layers to create query, key, and value vectors. Query, key, and value vectors may be fed through a linear layer; then, the query and key vectors may be multiplied using dot product matrix multiplication in order to produce a score matrix. Score matrix may determine the amount of focus for a word that should be put on other words (thus, each word may be a score that corresponds to other words in the time-step). The values in score matrix may be scaled down. As a nonlimiting example, score matrix may be divided by the square root of the dimension of the query and key vectors. In one or more embodiments, a softmax of the scaled scores in score matrix may be taken. The output of this softmax function may be called attention weights. Attention weights may be multiplied by your value vector to obtain an output vector, wherein the output vector may then be fed through a final linear layer.

With continued reference to FIG. 1, in order to use self-attention in a multi-headed attention computation, query, key, and value may be split into N vectors before applying self-attention. Each self-attention process may be called a "head". Each head may produce an output vector and each output vector from each head may be concatenated into a single vector. This single vector may then be fed through final linear layer discussed above. In theory, each head can learn something different from input, therefore giving the encoder model more representation power.

With continued reference to FIG. 1, encoder of transformer may include a residual connection. Residual connection may include adding the output from multi-headed attention to the positional input embedding. In one or more embodiments, an output from residual connection may go through a layer normalization. In one or more embodiments, a normalized residual output may be projected through a pointwise feed-forward network for further processing. Pointwise feed-forward network may include a couple of linear layers with a ReLU activation in between. Output may then be added to an input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In one or more embodiments, decoder may include two multi-headed attention layers. In one or more embodiments, decoder may be autoregressive. For the purposes of this disclosure, "autoregressive" means that the decoder takes in a list of previous outputs as inputs along with encoder outputs containing attention information from the input.

With continued reference to FIG. 1, in one or more embodiments, input to decoder may go through an embedding layer and positional encoding layer to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a nonlimiting example, when computing attention scores on the word "am", decoder should not have access to the word "fine" in "I am fine", because that word is a future word that was generated after. The word "am" should only have access to itself and the words before it. In one or more embodiments, this may be accomplished by implementing a look-ahead mask. Look ahead mask is a matrix of the same dimensions as a scaled attention score matrix that is filled with "Os" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when a softmax of this matrix is taken, negative infinities will be zeroed out; this leaves zero attention scores for "future tokens."

With continued reference to FIG. 1, second multi-headed attention layer may use encoder outputs as queries and keys and outputs from the first multi-headed attention layer as values. This process matches encoder's input to the decoder's input, allowing the decoder to decide which encoder input is relevant to put a focus on. An output from second multi-headed attention layer may be fed through a pointwise feedforward layer for further processing.

With continued reference to FIG. 1, an output of the pointwise feedforward layer may be fed through a final linear layer. This final linear layer may act as a classifier. This classifier may be as big as the number of classes that you have. For example, if you have 10,000 classes for 10,000 words, output of that classifier will be of size 10,000. Output of this classifier may be fed into a softmax layer which may serve to produce probability scores between zero and one. An index may be taken of the highest probability score in order to determine a predicted word.

With continued reference to FIG. 1, decoder may take this output and add it to decoder inputs. Decoder may continue decoding until a token is predicted. Decoder may stop decoding once it predicts an end token.

With continued reference to FIG. 1, in one or more embodiments, decoder may be stacked N layers high, with each layer taking in inputs from encoder and layers before it. Stacking layers may allow LLM to learn to extract and focus on different combinations of attention from its attention heads.

With continued reference to FIG. 1, LLM may receive an input. Input may include a string of one or more characters. Inputs may additionally include unstructured data. For example, input may include one or more words, a sentence, a paragraph, a thought, a query, and the like. For the purposes of this disclosure, a "query" is a string of characters that poses a question. In one or more embodiments, input may be received from a user device. User device may be any computing device that is used by a user. As nonlimiting examples, user device may include desktops, laptops, smartphones, tablets, and the like. In one or more embodiments, input may include any set of data associated with training and/or using LLM. As a nonlimiting example, input may be a prompt such as "what abnormalities are present in the attached ECG signal?"

With continued reference to FIG. 1, LLM may generate at least one annotation as output. At least one annotation may be any annotation as described herein. In one or more embodiments, LLM may include multiple sets of transformer architecture as described above. Output may include a textual output. For the purposes of this disclosure, "textual output" is an output comprising a string of one or more characters. Textual output may include, for example, a plurality of annotations for unstructured data. In one or more embodiments, textual output may include a phrase or sentence identifying the status of a user query. In one or more embodiments, textual output may include a sentence or plurality of sentences describing a response to user query. As a nonlimiting example, this may include restrictions, timing, advice, dangers, benefits, and the like.

With continued reference to FIG. 1, processor 116 is configured to highlight at least a biomedical feature 124 within the image 108 as a function of at least a distance metric 140. In one or more embodiments, highlighting at least a biomedical feature 124 within image 108 may comprise generating a color-coded heat map at one or more regions within the image. As a nonlimiting example, a large distance metric 140 may be associated with a first color, whereas a small distance metric 140 may be associated with a second color, wherein the first color is different from the second color. As another nonlimiting example, a plurality of distance metrics 136 a may be correlated with a plurality of colors, on a continuous scale. In one or more embodiments, highlighting at least a biomedical feature 124 may include overlaying color-coded heat map on top of image 108. Similarly, in one or more embodiments, processor 116 may be configured to apply suitable inclusion/exclusion criteria to generate a plurality of color-coded heat maps correlated to a plurality of hypotheses 144, and users may be able to toggle between two or more color-coded heat maps by selecting different hypotheses 144 through one or more user interfaces. As a nonlimiting example, the choice of color may be correlated with a level of confidence determined by apparatus 100 when validating one or more hypotheses 144; red may be used for a case with a high confidence level, whereas green may be used for a case with a low confidence level. Validation of at least a hypothesis 144 and level of confidence associated thereto may be consistent with any details disclosed in U.S. patent application Ser. No. 18/648, 059, filed on Apr. 26, 2024, and entitled "APPARATUS AND METHODS FOR GENERATING DIAGNOSTIC HYPOTHESES BASED ON BIOMEDICAL SIGNAL DATA", the entirety of which incorporated herein by reference. Additional details will be provided below in this disclosure through nonlimiting examples.

With continued reference to FIG. 1, apparatus 100 comprises a display device 160 communicatively connected to processor 116, wherein the display device 160 is configured to display at least a highlighted biomedical feature 124 within image 108. In one or more embodiments, apparatus 100 may further comprise a user interface, wherein generating color-coded heat map may include generating a plurality of color-coded regions as function of the at least a distance metric 140 and displaying, using display device 160, the plurality of color-coded regions. For the purposes of this disclosure, a "display device" is a device configured to show visual information. In some cases, display device 160 may include a liquid crystal display (LCD), a cathode ray tube (CRT), a plasma display, a light emitting diode (LED) display, and any combinations thereof. Display device 160 may include, but is not limited to, a smartphone, tablet, laptop, monitor, tablet, and the like. Display device 160 may include a separate device that includes a transparent screen configured to display computer-generated images and/or information. In one or more embodiments, display device 160 may be configured to visually present data through a user interface or a graphical user interface (GUI) to at least a user, wherein the user may interact with the data through the user interface or GUI, as described below. In one or more embodiments, a user may view GUI through display device 160. In one or more embodiments, display device 160 may be located on remote device, as described below. In one or more embodiments, display device 160 and image capture device 104 may be the same device or integrated within the same device, such as a smartphone or a tablet. Additional details will be provided below in this disclosure through nonlimiting examples.

With continued reference to FIG. 1, display device 160 may include a remote device. For the purposes of this disclosure, a "remote device" is a computer device separate and distinct from apparatus 100. For example, and without limitation, remote device may include a smartphone, a tablet, a laptop, a desktop computer, or the like. In one or more embodiments, remote device may be communicatively connected to apparatus 100 such as, for example, through network communication, through Bluetooth communication, and/or the like. In one or more embodiments, processor 116 may receive image 108 and/or initiate one or more of subsequent steps through remote device. In one or more embodiments, one or more inputs from one or more users may be submitted through a user interface, such as a GUI, embedded within remote device, as described below.

With continued reference to FIG. 1, in one or more embodiments, apparatus 100 may further comprise a user interface, wherein highlighting at least a biomedical feature 124 within image 108 comprises receiving, using the user interface, a user query 164 from a user, and highlighting, using the user interface, the at least a biomedical feature 124 within the image 108 as a function of the user query 164. For the purposes of this disclosure, a "user interface" is a means by which a user and a computer system interact, for example, using input devices and software. User interface may include a graphical user interface (GUI), command line interface (CLI), menu-driven user interface, touch user interface, voice user interface (VUI), form-based user interface, any combination thereof, or the like. In one or more embodiments, a user may interact with user interface using computing device distinct from and communicatively connected to processor 116, such as a smartphone, tablet, or the like operated by the user. User interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, GUI may include icons, menus, other visual indicators or representations (graphics), audio indicators such as primary notation, display information, and related user controls. Menu may contain a list of choices and may allow users to select one from them. A menu bar may be displayed horizontally across the screen as a pull-down menu. Menu may include a context menu that appears only when user performs a specific action. Files, programs, web pages, and the like may be represented using a small picture within GUI. In one or more embodiments, GUI may include a graphical visualization of a user profile and/or the like. In one or more embodiments, processor 116 may be configured to modify and/or update GUI as a function of at least an input or the like by populating a user interface data structure and visually presenting data through modification of the GUI.

With continued reference to FIG. 1, in one or more embodiments, GUI may contain one or more interactive elements. For the purposes of this disclosure, an "interactive element" is an element within GUI that allows for communication with processor 116 by one or more users. For example, and without limitation, interactive elements may include a plurality of tabs wherein selection of a particular tab, such as for example, by using a fingertip, may indicate to a system to perform a particular function and display the result through GUI. In one or more embodiments, interactive element may include tabs within GUI, wherein the selection of a particular tab may result in a particular function. In one or more embodiments, interactive elements may include words, phrases, illustrations, and the like to indicate a particular process that one or more users would like system to perform. A person of ordinary skill in the art, upon reviewing the entirety of this disclosure, will be aware of various ways in which user interfaces, GUIs, and/or elements thereof may be implemented and/or used as described in this disclosure.

With continued reference to FIG. 1, in one or more embodiments, processor 116 may be further configured to identify within medical repository 136 at least a second patient associated with at least a similar distance metric 140 and/or hypothesis 144, wherein a first set of statistical parameters 168 are extracted as a function of image 108, at least a second set of statistical parameters 168 are extracted as a function of at least an image associated with the at least a second patient, and identifying the at least a second patient comprises matching the first set of statistical parameters 168 with the at least a second set of statistical parameters 168 using a statistical model 172. For the purposes of this disclosure, "statistical parameters" are characteristics or metrics that describe how one data element or group of data elements compares to another data element or group of data elements. In some cases, a match between first set of statistical parameters 168 at least a second set of statistical parameters 168 may be determined as a function of one or more pre-determined criteria selected by one or more medical professionals. As a nonlimiting example, first set of statistical parameters 168 and second set of statistical parameters 168 may be considered a match when the two sets of statistical parameters 168 are within one standard deviation from each other, as described below. As a nonlimiting example, matching first set of statistical parameters 168 with at least a second set of statistical parameters 168 may involve a fuzzy set comparison, as described below.

With continued reference to FIG. 1, one or more embodiments, a large group of patients with a similar lifestyle or medical history may be combined into a cohort, wherein statistical parameters 168 of patients within the cohort may be combined and tallied to form statistical model 172.

Statistical model 172 may be described by one or more numerical indicators such as without limitation an average or mean, a median, a standard deviation, a variance, a range, or the like. "Statistical model" and "statistical distribution" may be used interchangeably throughout this disclosure. In one or more embodiments, statistical model 172 may be updated when its associated cohort or cohorts are filtered into one or more sub-cohorts as a function of one or more inclusion/exclusion criteria. As a nonlimiting example, one or more statistical parameters 168 associated with first patient may be compared to and/or located within statistical model 172 to help medical professional decide whether there is one or more abnormal biomedical features within image 108. For the purposes of this disclosure, an "abnormal biomedical feature" is biomedical feature 124 possessed by or associated with a minority of population and/or described by a numerical value that is different from a statistical average of the population, according to one or more cutoffs and/or pre-determined criteria. As a nonlimiting example, an abnormal biomedical feature may be specified as biomedical feature 124 possessed by or associated with less than 50% of the population and/or described by a numerical value that is at least two standard deviations away from statistical average. Implementation of embodiments described herein may be consistent with any detail disclosed in U.S. patent application Ser. No. 18/652,921, filed on May 2, 2024, and titled "AN APPARATUS AND METHOD FOR CLASSIFYING A USER TO A COHORT OF RETROSPECTIVEUSERS", the entirety of each of which is incorporated herein by reference.

Figure 2:
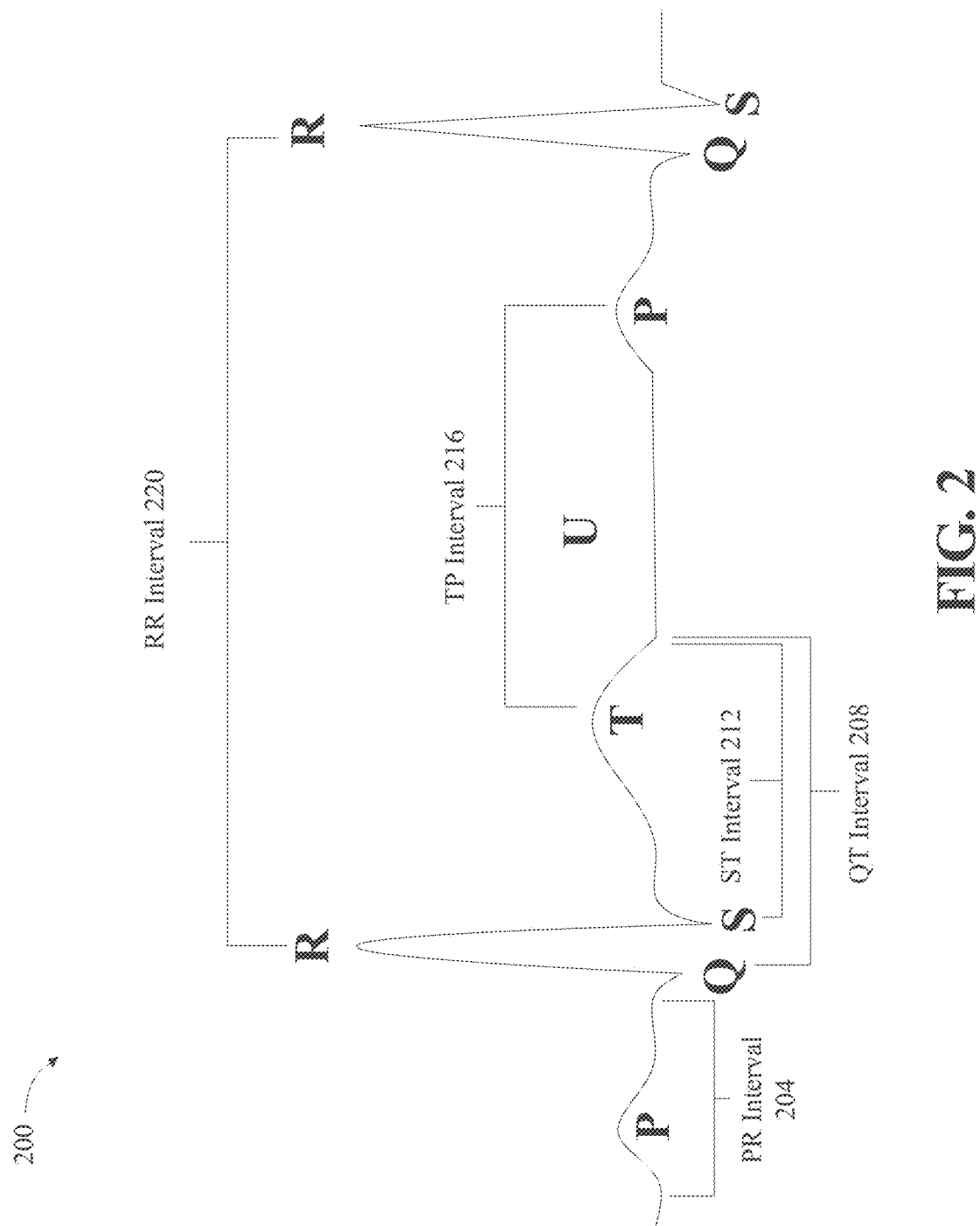
FIG. 2 is an exemplary embodiment of an electrocardiogram (ECG)

Referring now to FIG. 2, in one or more embodiments, biomedical data 112 contained within image 108 may include at least an ECG, an exemplary embodiment 200 of which is illustrated. ECG may include a plurality of features such as P-wave, Q-wave, R-wave, S-wave, QRS complex, and T wave, as well as a plurality of parameters such a PR interval 204, QT interval 208, ST interval 212, TP interval 216, RR interval 220, and the like. P-wave may reflect atrial depolarization (activation). For the purposes of this disclosure, a "PR interval" is the distance between the onset of P-wave to the onset of QRS complex. PR interval 204 may be assessed to determine whether impulse conduction from the atria to the ventricles is normal. PR interval 204 may be measured in seconds. For the purposes of this disclosure, a "QT interval" is a reflection of the total duration of ventricular depolarization and repolarization and is measured from the onset of QRS complex to the end of T-wave. The QT duration may be inversely related to heart rate; i.e., QT interval 208 may increase at slower heart rates and decrease at higher heart rates. Therefore, to determine whether QT interval 208 is within normal limits, it may be necessary to adjust for the heart rate. A heart rate-adjusted QT interval 208 is referred to as a corrected QT interval 208 (QTc interval). A long QTc interval may indicate an increased risk of ventricular arrhythmias. The QTc interval may be in the range of 0.36 to 0.44 seconds. For the purposes of this disclosure, an "RR interval" is the time between two consecutive R waves. For the purposes of this disclosure, a "QRS complex" is a representation of the depolarization (activation) of ventricles depicted between Q-, R- and S-waves, although it may not always display all three waves. Since the electrical vector generated by the left ventricle is usually many times larger than the vector generated by the right ventricle, QRS complex is a reflection of left ventricular depolarization.

With continued reference to FIG. 2, for the purposes of this disclosure, an "ST interval" is the segment of ECG that starts at the end of QRS complex and extends to the beginning of T wave; it represents the early part of ventricular repolarization. ST segment may be relatively isoelectric, meaning it is at the baseline, with minimal elevation or depression. The normal duration of ST interval 212 is usually around 0.12 seconds. For the purposes of this disclosure, a "TP interval" is the segment of ECG that extends from the end of T wave to the beginning of the next P wave; it represents the time when the ventricles are fully repolarized and are in a resting state. The duration of TP interval 216 may vary but is typically short, as it may represent the brief pause between cardiac cycles. Significant deviations may be associated with certain conditions affecting repolarization. For the purposes of this disclosure, an "RR interval" is the time between two consecutive R waves of ECG; it may represent the duration of one cardiac cycle, encompassing both atrial and ventricular depolarization and repolarization. RR interval 220 may be measured in seconds and can be used to calculate heart rate (beats per minute) using $$\text{heart rate} = \frac{60}{RR \text{ Interval}}$$

(in seconds). The intervals described above may be used to determine a ventricular rate, i.e., the number of ventricular contractions (heartbeats) that occur in one minute, which may be closely related to RR interval 220 of ECG, as the RR interval 220 represents the time between two consecutive ventricular contractions.

Figure 3:
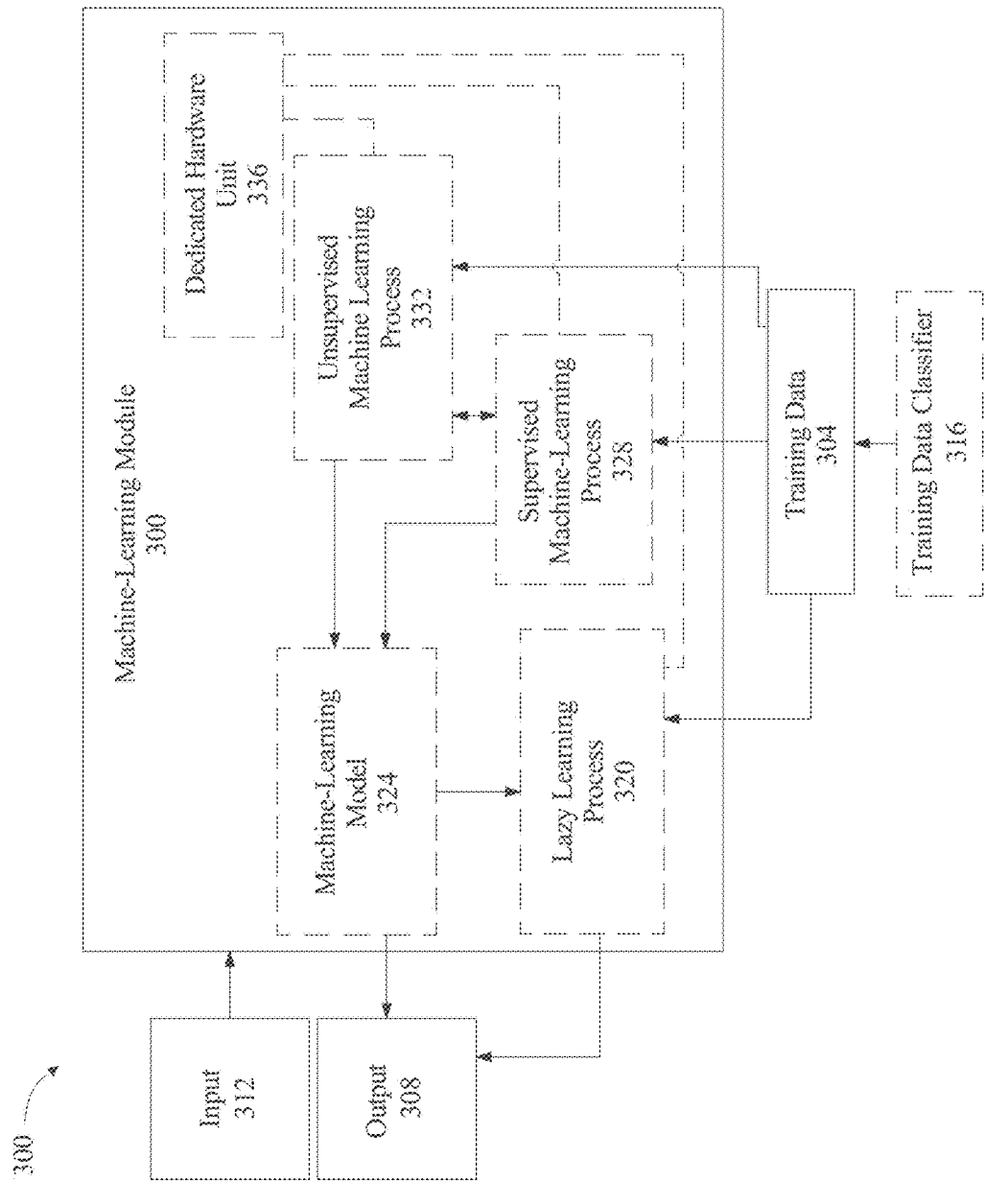
FIG. 3 is a block diagram of an exemplary embodiment of a machine learning process.

Referring now to FIG. 3, an exemplary embodiment of a machine learning module 300 that may perform one or more machine learning processes as described above is illustrated. Machine learning module may perform determinations, classification, and/or analysis steps, methods, processes, or the like as described in this disclosure using machine learning processes. For the purposes of this disclosure, a "machine learning process" is an automated process that uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are pre-determined by user and written in a programming language.

With continued reference to FIG. 3, "training data", for the purposes of this disclosure, are data containing correlations that a machine learning process may use to model relationships between two or more categories of data elements. For instance, and without limitation, training data 304 may include a plurality of data entries, also known as "training examples", each entry representing a set of data elements that were recorded, received, and/or generated together. Data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine learning processes as described in further detail below. Training data 304 may be formatted and/or organized by categories of data elements, for instance by associating data elements with one or more descriptors corresponding to categories of data elements. As a nonlimiting example, training data 304 may include data entered in standardized forms by persons or processes, such that entry of a given data element within a given field in a given form may be mapped to one or more descriptors of categories. Elements in training data 304 may be linked to descriptors of categories by tags, tokens, or other data elements. For instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

With continued reference to FIG. 3, alternatively or additionally, training data 304 may include one or more elements that are uncategorized; that is, training data 304 may not be formatted or contain descriptors for some elements of data. Machine learning algorithms and/or other processes may sort training data 304 according to one or more categorizations using, for instance, natural language processing algorithms, tokenization, detection of correlated values in raw data, and the like; categories may be generated using correlation and/or other processing algorithms. As a nonlimiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 304 to be made applicable for two or more distinct machine learning algorithms as described in further detail below. Training data 304 used by machine learning module 300 may correlate any input data as described in this disclosure to any output data as described in this disclosure. As a nonlimiting illustrative example, inputs may include plurality of images containing biomedical data 112, whereas outputs may include plurality of biomedical features 124.

With continued reference to FIG. 3, training data 304 may be filtered, sorted, and/or selected using one or more supervised and/or unsupervised machine learning processes and/or models as described in further detail below; such processes and/or models may include without limitation a training data classifier 316. For the purposes of this disclosure, a "classifier" is a machine learning model, such as a data structure representing and/or using a mathematical model, neural net, or a program generated by a machine learning algorithm, known as a "classification algorithm", that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine learning module 300 may generate a classifier using a classification algorithm. For the purposes of this disclosure, a "classification algorithm" is a process wherein a computing device and/or any module and/or component operating therein derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, training data classifier 316 may classify elements of training data to a plurality of cohorts as a function of certain anatomic and/or demographic traits.

With continued reference to FIG. 3, machine learning module 300 may be configured to generate a classifier using a naive Bayes classification algorithm. Naive Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as $P(A/B)=P(B/A) \times P(A)=P(B)$, where $P(A/B)$ is the probability of hypothesis A given data B, also known as posterior probability; $P(B/A)$ is the probability of data B given that the hypothesis A was true; $P(A)$ is the probability of hypothesis A being true regardless of data, also known as prior probability of A; and $P(B)$ is the probability of the data regardless of the hypothesis. A naive Bayes algorithm may be generated by first transforming training data into a frequency table. Machine learning module 300 may then calculate a likelihood table by calculating probabilities of different data entries and classification labels. Machine learning module 300 may utilize a naive Bayes equation to calculate a posterior probability for each class. A class containing the highest posterior probability is the outcome of prediction. Naive Bayes classification algorithm may include a gaussian model that follows a normal distribution. Naive Bayes classification algorithm may include a multinomial model that is used for discrete counts. Naive Bayes classification algorithm may include a Bernoulli model that may be utilized when vectors are binary.

With continued reference to FIG. 3, machine learning module 300 may be configured to generate a classifier using a k-nearest neighbors (KNN) algorithm. For the purposes of this disclosure, a "k-nearest neighbors algorithm" is or at least includes a classification method that utilizes feature similarity to analyze how closely out-of-sample features resemble training data 304 and to classify input data to one or more clusters and/or categories of features as represented in training data 304; this may be performed by representing both training data 304 and input data in vector forms and using one or more measures of vector similarity to identify classifications within training data 304 and determine a classification of input data. K-nearest neighbors algorithm may include specifying a k-value, or a number directing the classifier to select the k most similar entries of training data 304 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a nonlimiting example, an initial heuristic may include a ranking of associations between inputs 312 and elements of training data 304. Heuristic may include selecting some number of highest-ranking associations and/or training data elements.

With continued reference to FIG. 3, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least 2. Each value of n-tuple of values may represent a measurement or other quantitative value associated with a given category of data or attribute, examples of which are provided in further detail below. A vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent when their directions and/or relative quantities of values are the same; thus, as a nonlimiting example, a vector represented as [5, 10, 15] may be treated as equivalent, for the purposes of this disclosure, as a vector represented as [1, 2, 3]. Vectors may be more similar where their directions are more similar, and more different where their directions are more divergent. However, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized", or divided by a "length" attribute, such as a length attribute 1 as derived using a Pythagorean norm:

$$l = \sqrt{\sum_{i=0}^{n} a_i^2},$$

where $a_i$ is attribute number of vector i. Scaling and/or normalization may function to make vector comparison independent of absolute quantities of attributes, while preserving any dependency on similarity of attributes. This may, for instance, be advantageous where cases represented in training data 304 are represented by different quantities of samples, which may result in proportionally equivalent vectors with divergent values.

With continued reference to FIG. 3, training examples for use as training data may be selected from a population of potential examples according to cohorts relevant to an analytical problem to be solved, a classification task, or the like. Alternatively or additionally, training data 304 may be selected to span a set of likely circumstances or inputs for a machine learning model and/or process to encounter when deployed. For instance, and without limitation, for each category of input data to a machine learning model and/or process that may exist in a range of values in a population of phenomena such as images, user data, process data, physical data, or the like, a computing device, processor 116, and/or machine learning module 300 may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to user, so that a process can detect, automatically or via user input, one or more values that are not included in the set of training examples. Computing device, processor 116, and/or machine learning module 300 may automatically generate a missing training example. This may be done by receiving and/or retrieving a missing input and/or output value and correlating the missing input and/or output value with a corresponding output and/or input value collocated in a data record with the retrieved value, provided by user, another device, or the like.

With continued reference to FIG. 3, computing device, processor 116, and/or machine learning module 300 may be configured to preprocess training data 304. For the purposes of this disclosure, "preprocessing" training data is a process that transforms training data from a raw form to a format that can be used for training a machine learning model. Preprocessing may include sanitizing, feature selection, feature scaling, data augmentation and the like.

With continued reference to FIG. 3, computing device, processor 116, and/or machine learning module 300 may be configured to sanitize training data. For the purposes of this disclosure, "sanitizing" training data is a process whereby training examples that interfere with convergence of a machine learning model and/or process are removed to yield a useful result. For instance, and without limitation, a training example may include an input and/or output value that is an outlier from typically encountered values, such that a machine learning algorithm using the training example will be skewed to an unlikely range of input 312 and/or output 308; a value that is more than a threshold number of standard deviations away from an average, mean, or expected value, for instance, may be eliminated. Alternatively or additionally, one or more training examples may be identified as having poor-quality data, where "poor-quality" means having a signal-to-noise ratio below a threshold value. In one or more embodiments, sanitizing training data may include steps such as removing duplicative or otherwise redundant data, interpolating missing data, correcting data errors, standardizing data, identifying outliers, and/or the like. In one or more embodiments, sanitizing training data may include algorithms that identify duplicate entries or spell-check algorithms.

With continued reference to FIG. 3, in one or more embodiments, images used to train an image classifier or other machine learning model and/or process that takes images as inputs 312 or generates images as outputs 308 may be rejected if image quality is below a threshold value. For instance, and without limitation, computing device, processor 116, and/or machine learning module 300 may perform blur detection. Elimination of one or more blurs may be performed, as a nonlimiting example, by taking Fourier transform or a Fast Fourier Transform (FFT) of image and analyzing a distribution of low and high frequencies in the resulting frequency-domain depiction of the image. Numbers of high-frequency values below a threshold level may indicate blurriness. As a further nonlimiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of image, based on the hypothesis that rapid changes indicate sharp edges in the image, and thus are indicative of a lower degree of blurriness. Blur detection may be performed using a wavelet-based operator, which uses coefficients of a discrete wavelet transform to describe the frequency and spatial content of images. Blur detection may be performed using statistics-based operators that take advantage of several image statistics as texture descriptors in order to compute a focus level. Blur detection may be performed by using discrete cosine transform (DCT) coefficients in order to compute a focus level of an image from its frequency content.

With continued reference to FIG. 3, computing device, processor 116, and/or machine learning module 300 may be configured to precondition one or more training examples. For instance, and without limitation, where a machine learning model and/or process has one or more inputs 312 and/or outputs 308 requiring, transmitting, or receiving a certain number of bits, samples, or other units of data, one or more elements of training examples to be used as or compared to inputs 312 and/or outputs 308 may be modified to have such a number of units of data. In one or more embodiments, computing device, processor 116, and/or machine learning module 300 may convert a smaller number of units, such as in a low pixel count image, into a desired number of units by upsampling and interpolating. As a nonlimiting example, a low pixel count image may have 100 pixels, whereas a desired number of pixels may be 136. Processor 116 may interpolate the low pixel count image to convert 100 pixels into 136 pixels. It should also be noted that one of ordinary skill in the art, upon reading the entirety of this disclosure, would recognize the various methods to interpolate a smaller number of data units such as samples, pixels, bits, or the like to a desired number of such units. In one or more embodiments, a set of interpolation rules may be trained by sets of highly detailed inputs 312 and/or outputs 308 and corresponding inputs 312 and/or outputs 308 downsampled to smaller numbers of units, and a neural network or another machine learning model that is trained to predict interpolated pixel values using the training data 304. As a nonlimiting example, a sample input 312 and/or output 308, such as a sample picture, with sample-expanded data units (e.g., pixels added between the original pixels) may be input to a neural network or machine learning model and output a pseudo replica sample picture with dummy values assigned to pixels between the original pixels based on a set of interpolation rules. As a nonlimiting example, in the context of an image classifier, a machine learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, computing device, processor 116, and/or machine learning module 300 may utilize sample expander methods, a low-pass filter, or both. For the purposes of this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor 116, and/or machine learning module 300 may use averaging, such as luma or chroma averaging in images, to fill in data units in between original data units.

With continued reference to FIG. 3, in one or more embodiments, computing device, processor 116, and/or machine learning module 300 may downsample elements of a training example to a desired lower number of data elements. As a nonlimiting example, a high pixel count image may contain 256 pixels, however a desired number of pixels may be 136. Processor 116 may downsample the high pixel count image to convert 256 pixels into 136 pixels. In one or more embodiments, processor 116 may be configured to perform downsampling on data. Downsampling, also known as decimation, may include removing every $N^{th}$ entry in a sequence of samples, all but every $N^{th}$ entry, or the like, which is a process known as "compression" and may be performed, for instance by an N-sample compressor implemented using hardware or software. Anti-aliasing and/or anti-imaging filters, and/or low-pass filters, may be used to eliminate side effects of compression.

With continued reference to FIG. 3, feature selection may include narrowing and/or filtering training data 304 to exclude features and/or elements, or training data including such elements that are not relevant to a purpose for which a trained machine learning model and/or algorithm is being trained, and/or collection of features, elements, or training data including such elements based on relevance to or utility for an intended task or purpose for which a machine learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, wherein a difference between each value, X, and a minimum value, $X_{min}$, in a set or subset of values is divided by a range of values, $X_{max} - X_{min}$, in the set or subset:

$$X_{new} = \frac{X - X_{min}}{X_{max} - X_{min}}.$$

Feature scaling may include mean normalization, wherein a difference between each value, X, and a mean value of a set and/or subset of values, $X_{mean}$, is divided by a range of values, $X_{max} - X_{min}$, in the set of subset:

$$X_{new} = \frac{X - X_{mean}}{X_{max} - X_{min}}.$$

Feature scaling may include standardization, wherein a difference between X and $X_{mean}$ is divided by a standard deviation, σ, of a set or subset of values:

$$X_{new} = \frac{X - X_{mean}}{\sigma}.$$

Feature scaling may be performed using a median value of a set or subset, $X_{median}$, and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

A Person of ordinary skill in the art, upon reviewing the entirety of this disclosure, will be aware of various alternative or additional approaches that may be used for feature scaling.

With continued reference to FIG. 3, computing device, processor 116, and/or machine learning module 300 may be configured to perform one or more processes of data augmentation. For the purposes of this disclosure, "data augmentation" is a process that adds data to a training data 304 using elements and/or entries already in the dataset. Data augmentation may be accomplished, without limitation, using interpolation, generation of modified copies of existing entries and/or examples, and/or one or more generative artificial intelligence (AI) processes, for instance using deep neural networks and/or generative adversarial networks. Generative processes may be referred to alternatively in this context as "data synthesis" and as creating "synthetic data". Augmentation may include performing one or more transformations on data, such as geometric, color space, affine, brightness, cropping, and/or contrast transformations of images.

With continued reference to FIG. 3, machine learning module 300 may be configured to perform a lazy learning process and/or protocol 320. For the purposes of this disclosure, a "lazy learning" process and/or protocol is a process whereby machine learning is conducted upon receipt of input 312 to be converted to output 308 by combining the input 312 and training data 304 to derive the algorithm to be used to produce the output 308 on demand. A lazy learning process may alternatively be referred to as a "lazy loading" or "call-when-needed" process and/or protocol. For instance, an initial set of simulations may be performed to cover an initial heuristic and/or "first guess" at an output 308 and/or relationship. As a nonlimiting example, an initial heuristic may include a ranking of associations between inputs 312 and elements of training data 304. Heuristic may include selecting some number of highest-ranking associations and/or training data 304 elements. Lazy learning may implement any suitable lazy learning algorithm, including without limitation a k-nearest neighbors algorithm, a lazy naive Bayes algorithm, or the like. A person of ordinary skill in the art, upon reviewing the entirety of this disclosure, will be aware of various lazy learning algorithms that may be applied to generate outputs as described in this disclosure, including without limitation lazy learning applications of machine learning algorithms as described in further detail below.

With continued reference to FIG. 3, alternatively or additionally, machine learning processes as described in this disclosure may be used to generate machine learning models 324. A "machine learning model", for the purposes of this disclosure, is a data structure representing and/or instantiating a mathematical and/or algorithmic representation of a relationship between inputs 312 and outputs 308, generated using any machine learning process including without limitation any process described above, and stored in memory. An input 312 is submitted to a machine learning model 324 once created, which generates an output 308 based on the relationship that was derived. For instance, and without limitation, a linear regression model, generated using a linear regression algorithm, may compute a linear combination of input data using coefficients derived during machine learning processes to calculate an output datum. As a further nonlimiting example, a machine learning model 324 may be generated by creating an artificial neural network, such as a convolutional neural network comprising an input layer of nodes, one or more intermediate layers, and an output layer of nodes. Connections between nodes may be created by "training" the network, in which elements from a training data 304 are applied to the input nodes, and a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, as described in detail below.

With continued reference to FIG. 3, machine learning module 300 may perform at least a supervised machine learning process 328. For the purposes of this disclosure, a "supervised" machine learning process is a process with algorithms that receive training data 304 relating one or more inputs 312 to one or more outputs 308, and seek to generate one or more data structures representing and/or instantiating one or more mathematical relations relating input 312 to output 308, where each of the one or more mathematical relations is optimal according to some criterion specified to the algorithm using some scoring function. For instance, a supervised learning algorithm may include inputs 312 described above as inputs, and outputs 308 described above as outputs, and a scoring function representing a desired form of relationship to be detected between inputs 312 and outputs 308. Scoring function may, for instance, seek to maximize the probability that a given input 312 and/or combination thereof is associated with a given output 308 to minimize the probability that a given input 312 is not associated with a given output 308. Scoring function may be expressed as a risk function representing an "expected loss" of an algorithm relating inputs 312 to outputs 308, where loss is computed as an error function representing a degree to which a prediction generated by the relation is incorrect when compared to a given input-output pair provided in training data 304. Supervised machine learning processes may include classification algorithms as defined above. A person of ordinary skill in the art, upon reviewing the entirety of this disclosure, will be aware of various possible variations of at least a supervised machine learning process 328 that may be used to determine a relation between inputs and outputs.

With continued reference to FIG. 3, training a supervised machine learning process may include, without limitation, iteratively updating coefficients, biases, and weights based on an error function, expected loss, and/or risk function. For instance, an output 308 generated by a supervised machine learning model 328 using an input example in a training example may be compared to an output example from the training example; an error function may be generated based on the comparison, which may include any error function suitable for use with any machine learning algorithm described in this disclosure, including a square of a difference between one or more sets of compared values or the like. Such an error function may be used in turn to update one or more weights, biases, coefficients, or other parameters of a machine learning model through any suitable process including without limitation gradient descent processes, least-squares processes, and/or other processes described in this disclosure. This may be done iteratively and/or recursively to gradually tune such weights, biases, coefficients, or other parameters. Updates may be performed in neural networks using one or more back-propagation algorithms. Iterative and/or recursive updates to weights, biases, coefficients, or other parameters as described above may be performed until currently available training data 304 are exhausted and/or until a convergence test is passed. For the purposes of this disclosure, a "convergence test" is a test for a condition selected to indicate that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

With continued reference to FIG. 3, a computing device, processor 116, and/or machine learning module 300 may be configured to perform method, method step, sequence of method steps, and/or algorithm described in reference to this figure, in any order and with any degree of repetition. For instance, computing device, processor 116, and/or machine learning module 300 may be configured to perform a single step, sequence, and/or algorithm repeatedly until a desired or commanded outcome is achieved; repetition of a step or a sequence of steps may be performed iteratively and/or recursively using outputs 308 of previous repetitions as inputs 312 to subsequent repetitions, aggregating inputs 312 and/or outputs 308 of repetitions to produce an aggregate result, reduction or decrement of one or more variables such as global variables, and/or division of a larger processing task into a set of iteratively addressed smaller processing tasks. A computing device, processor 116, apparatus 100, or machine learning module 300 may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 3, machine learning process may include at least an unsupervised machine learning process 332. For the purposes of this disclosure, an unsupervised machine learning process is a process that derives inferences in datasets without regard to labels. As a result, an unsupervised machine learning process 332 may be free to discover any structure, relationship, and/or correlation provided in the data. Unsupervised processes 332 may not require a response variable, may be used to find interesting patterns and/or inferences between variables, to determine a degree of correlation between two or more variables, or the like.

With continued reference to FIG. 3, machine learning module 300 may be designed and configured to create machine learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include an elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to a person of ordinary skill in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought. Similar methods to those described above may be applied to minimize error functions, as will be apparent to a person of ordinary skill in the art upon reviewing the entirety of this disclosure.

With continued reference to FIG. 3, machine learning algorithms may include, without limitation, linear discriminant analysis. Machine learning algorithm may include quadratic discriminant analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors algorithms. Machine learning algorithms may include various forms of latent space regularization such as variational regularization. Machine learning algorithms may include Gaussian processes such as Gaussian Process Regression. Machine learning algorithms may include cross-decomposition algorithms, including partial least squares and/or canonical correlation analysis. Machine learning algorithms may include naive Bayes methods. Machine learning algorithms may include algorithms based on decision trees, such as decision tree classification or regression algorithms. Machine learning algorithms may include ensemble methods such as bagging meta-estimator, forest of randomized trees, AdaBoost, gradient tree boosting, and/or voting classifier methods. Machine learning algorithms may include neural net algorithms, including convolutional neural net processes.

With continued reference to FIG. 3, a machine learning model and/or process may be deployed or instantiated by incorporation into a program, apparatus, system, and/or module. For instance, and without limitation, a machine learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit, to represent a number according to any suitable encoding system including twos complement or the like, or may be stored in any volatile and/or non-volatile memory. Similarly, mathematical operations and input 312 and/or output 308 of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine learning process and/or model, including without limitation any combination of production and/or configuration of non-reconfigurable hardware elements, circuits, and/or modules such as without limitation application-specific integrated circuits (ASICs), production and/or configuration of reconfigurable hardware elements, circuits, and/or modules such as without limitation field programmable gate arrays (FPGAs), production and/or configuration of non-reconfigurable and/or non-rewritable memory elements, circuits, and/or modules such as without limitation non-rewritable read-only memory (ROM), other memory technology described in this disclosure, and/or production and/or configuration of any computing device and/or component thereof as described in this disclosure. Such deployed and/or instantiated machine learning model and/or algorithm may receive inputs 312 from any other process, module, and/or component described in this disclosure, and produce outputs 308 to any other process, module, and/or component described in this disclosure.

With continued reference to FIG. 3, any process of training, retraining, deployment, and/or instantiation of any machine learning model and/or algorithm may be performed and/or repeated after an initial deployment and/or instantiation to correct, refine, and/or improve the machine learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs 308 of machine learning models and/or algorithms, and/or errors and/or error functions thereof, to any thresholds, convergence tests, or the like, and/or may compare outputs 308 of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 3, retraining and/or additional training may be performed using any process for training described above, using any currently or previously deployed version of a machine learning model and/or algorithm as a starting point. Training data for retraining may be collected, preconditioned, sorted, classified, sanitized, or otherwise processed according to any process described in this disclosure. Training data 304 may include, without limitation, training examples including inputs 312 and correlated outputs 308 used, received, and/or generated from any version of any system, module, machine learning model or algorithm, apparatus, and/or method described in this disclosure. Such examples may be modified and/or labeled according to user feedback or other processes to indicate desired results, and/or may have actual or measured results from a process being modeled and/or predicted by system, module, machine learning model or algorithm, apparatus, and/or method as "desired" results to be compared to outputs 308 for training processes as described above. Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

With continued reference to FIG. 3, one or more processes or algorithms described above may be performed by at least a dedicated hardware unit 336. For the purposes of this disclosure, a "dedicated hardware unit" is a hardware component, circuit, or the like, aside from a principal control circuit and/or processor 116 performing method steps as described in this disclosure, that is specifically designated or selected to perform one or more specific tasks and/or processes described in reference to this figure, such as without limitation preprocessing and/or sanitization of training data and/or training a machine learning algorithm and/or model. Dedicated hardware unit 336 may include, without limitation, a hardware unit that can perform iterative or massed calculations, such as matrix-based calculations to update or tune parameters, weights, coefficients, and/or biases of machine learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously, in parallel, and/or the like. Such dedicated hardware units 336 may include, without limitation, graphical processing units (GPUs), dedicated signal processing modules, field programmable gate arrays (FPGA), other reconfigurable hardware that has been configured to instantiate parallel processing units for one or more specific tasks, or the like. Computing device, processor 116, apparatus 100, or machine learning module 300 may be configured to instruct one or more dedicated hardware units 336 to perform one or more operations described herein, such as evaluation of model and/or algorithm outputs, one-time or iterative updates to parameters, coefficients, weights, and/or biases, vector and/or matrix operations, and/or any other operations described in this disclosure.

Figure 4:
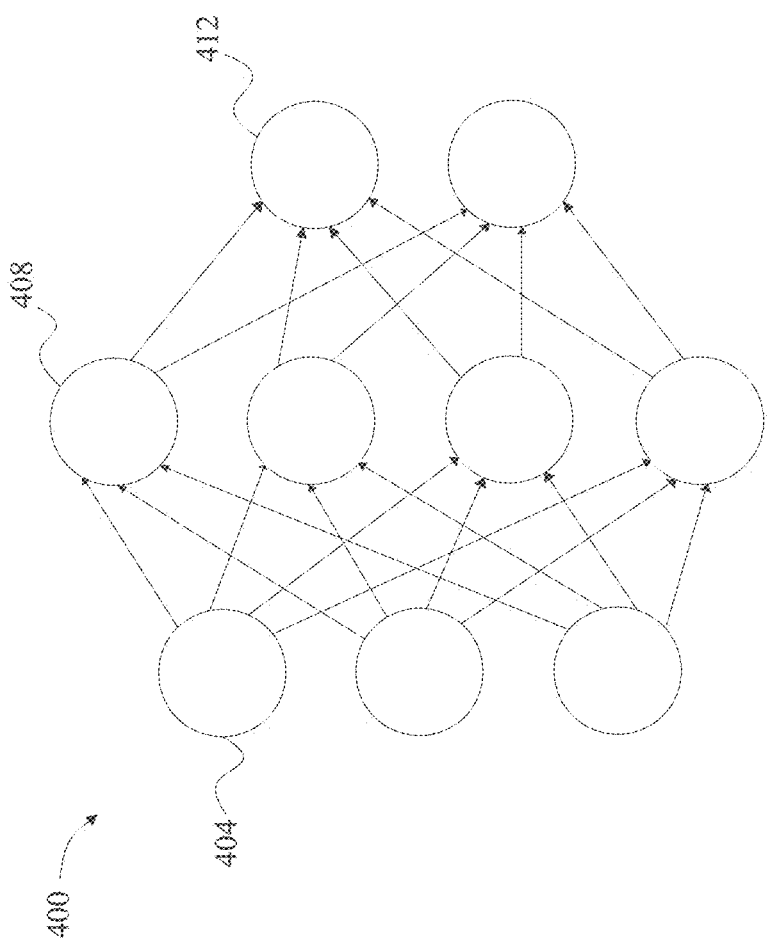
FIG. 4 is a block diagram of an exemplary embodiment of a neural network.

Referring now to FIG. 4, an exemplary embodiment of neural network 400 is illustrated. For the purposes of this disclosure, a neural network or artificial neural network is a network of "nodes" or data structures having one or more inputs, one or more outputs, and a function determining outputs based on inputs. Such nodes may be organized in a network, such as without limitation a convolutional neural network, including an input layer of nodes 404, at least an intermediate layer of nodes 408, and an output layer of nodes 412. Connections between nodes may be created via the process of "training" neural network 400, in which elements from a training dataset are applied to the input nodes, and a suitable training algorithm (such as Levenberg-Marquardt, conjugate gradient, simulated annealing, or other algorithms) is then used to adjust the connections and weights between nodes in adjacent layers of the neural network 400 to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further nonlimiting example, neural network 400 may include a convolutional neural network comprising an input layer of nodes 404, one or more intermediate layers of nodes 408, and an output layer of nodes 412. For the purposes of this disclosure, a "convolutional neural network" is a type of neural network 400 in which at least one hidden layer is a convolutional layer that convolves inputs to that layer with a subset of inputs known as a "kernel", along with one or more additional layers such as pooling layers, fully connected layers, and the like.

Figure 5:
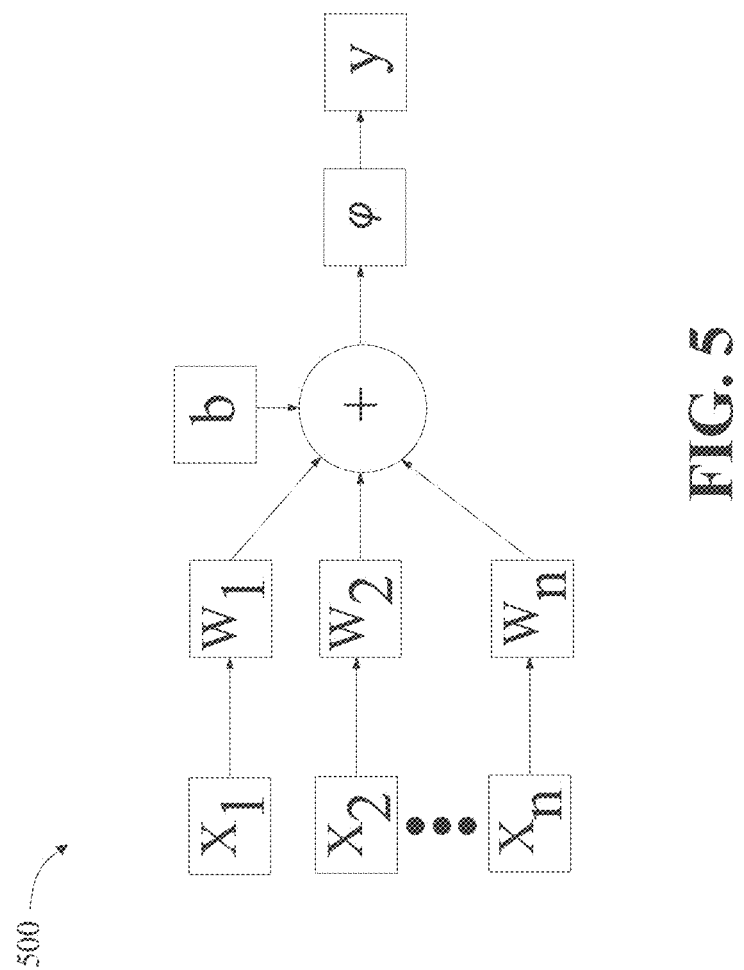
FIG. 5 is a block diagram of an exemplary embodiment of a node of a neural network.

Referring now to FIG. 5, an exemplary embodiment of a node 500 of neural network 400 is illustrated. Node 500 may include, without limitation, a plurality of inputs, $x_i$, that may receive numerical values from inputs to neural network 400 containing the node 500 and/or from other nodes 500. Node 500 may perform one or more activation functions to produce its output given one or more inputs, such as without limitation computing a binary step function comparing an input to a threshold value and outputting either a logic 1 or logic 0 output or its equivalent, a linear activation function whereby an output is directly proportional to input, and/or a nonlinear activation function wherein the output is not proportional to the input. Nonlinear activation functions may include, without limitation, a sigmoid function of the form $$f(x) = \frac{1}{1 - e^{-x}}$$

given input x, a tanh (hyperbolic tangent) function of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some value of a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$, that may be used as activation functions. As a nonlimiting and illustrative example, node 500 may perform a weighted sum of inputs using weights, $w_i$, that are multiplied by respective inputs, $x_i$. Additionally or alternatively, a bias b may be added to the weighted sum of the inputs such that an offset is added to each unit in a neural network layer that is independent of the input to the layer. The weighted sum may then be input into a function, φ, which may generate one or more outputs, y. Weight, $w_i$, applied to an input, $x_i$, may indicate whether the input is "excitatory", indicating that it has strong influence on the one or more outputs, y, for instance by the corresponding weight having a large numerical value, or "inhibitory", indicating it has a weak influence on the one more outputs, y, for instance by the corresponding weight having a small numerical value. The values of weights, $w_i$, may be determined by training neural network 400 using training data, which may be performed using any suitable process as described above.

Figure 6:
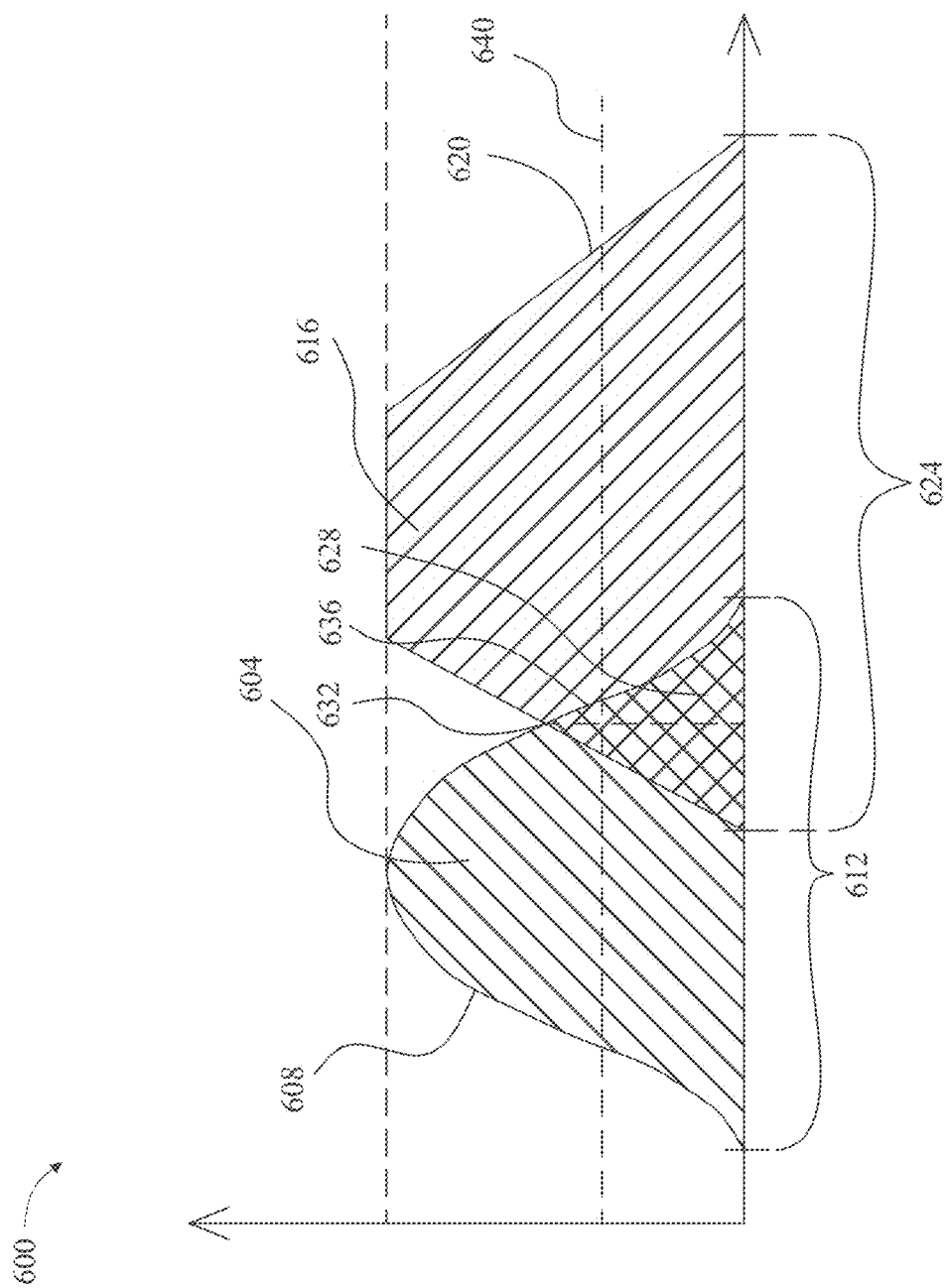
FIG. 6 is an illustration of an exemplary embodiment of fuzzy set comparison.

Referring now to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within the first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

A person of ordinary skill in the art, upon reviewing the entirety of this disclosure, will be aware of various alternative or additional membership functions that may be used consistently with this disclosure.

With continued reference to FIG. 6, in one or more embodiments, first fuzzy set 604 may represent any value or combination of values as described above, including output from one or more machine learning models. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a nonlimiting example, represent a degree of match between first fuzzy set 604 and second fuzzy set 616, and/or single values therein with each other or with either set, which is sufficient for purposes of the matching process; for instance, threshold 640 may indicate a sufficient degree of overlap between an output from one or more machine learning models. Alternatively or additionally, each threshold 640 may be tuned by a machine learning and/or statistical process, for instance and without limitation as described in further detail in this disclosure.

With continued reference to FIG. 6, in one or more embodiments, a degree of match between fuzzy sets may be used to classify plurality of biomedical data 112, such as one or more ECGs and/or one or more time series data within statistical model 172, and/or to identify at least an abnormal biomedical feature, as described above in this disclosure. In one or more embodiments, a degree of match between fuzzy sets may be used to identify at least a second patient associated with at least a similar distance metric 140 and/or hypothesis 144 by matching first set of statistical parameters 168 with at least a second set of statistical parameters 168, as described above in this disclosure. As a nonlimiting example, if one or more biomedical features within one or more biomedical data are associated with a fuzzy set that matches a fuzzy set of a cohort by having a degree of overlap exceeding a threshold, computing device may classify the biomedical data as belonging to that cohort. Where multiple fuzzy matches are performed, degrees of match for each respective fuzzy set may be computed and aggregated through, for instance, addition, averaging, or the like, to determine an overall degree of match.

With continued reference to FIG. 6, in one or more embodiments, one or more biomedical data 112 may be compared to multiple fuzzy sets of multiple cohorts. As a nonlimiting example, one or more biomedical features 124 or similar parameters within one or more biomedical data 112 may be represented by a fuzzy set that is compared to each of the multiple fuzzy sets of multiple cohorts, and a degree of overlap exceeding a threshold between the fuzzy set representing the biomedical data 112 and any of the multiple fuzzy sets representing multiple cohorts may cause computing device to classify the biomedical data 112 as belonging to that cohort. As a nonlimiting example, there may be two fuzzy sets representing two cohorts, cohort A and cohort B. Cohort A may have a cohort A fuzzy set, cohort B may have a cohort B fuzzy set, and biomedical data 112 may have a biomedical data fuzzy set. Computing device may compare biomedical data fuzzy set with each of cohort A fuzzy set and cohort B fuzzy set, as described above, and classify biomedical data 112 to either, both, or neither of cohort A fuzzy set and cohort B fuzzy set. Machine learning methods as described throughout this disclosure may, in a nonlimiting example, generate coefficients used in fuzzy set equations as described above, such as without limitation x, c, and σ of a Gaussian set as described above, as outputs of machine learning methods. Likewise, biomedical data 112 may be used indirectly to determine a fuzzy set, as biomedical data fuzzy set may be derived from outputs of one or more machine learning models that take biomedical data 112 directly or indirectly as inputs.

Figure 7:
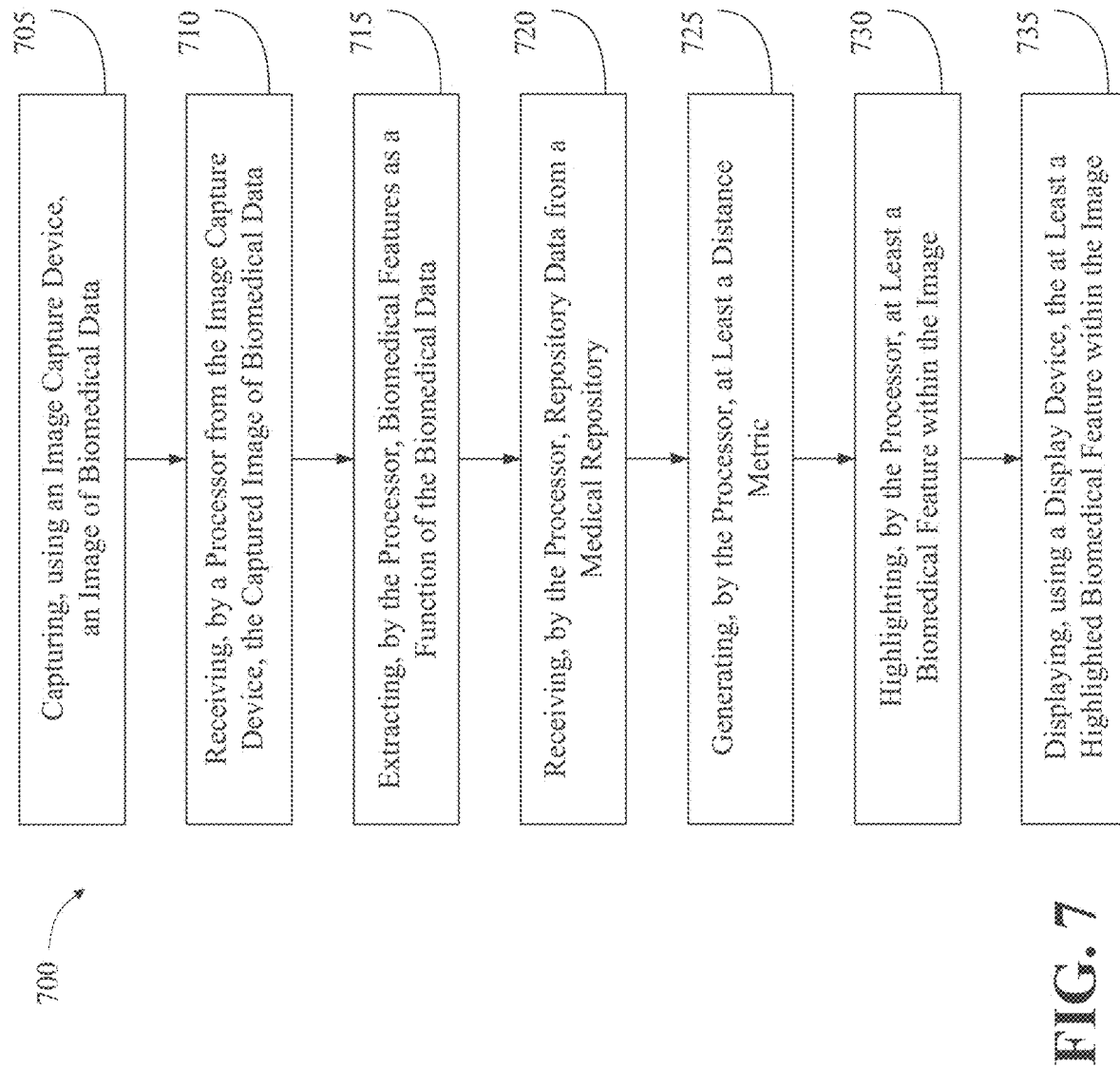
FIG. 7 is an exemplary flow diagram illustrating a method for identification of abnormal biomedical features within images of biomedical data.

Referring now to FIG. 7, an exemplary embodiment of a method 700 for identifying abnormal biomedical features within images of biomedical data is described.

With continued reference to FIG. 7, at step 705, method 700 includes capturing, using image capture device 104, image 108 of biomedical data 112 pertaining to a first patient. This step may be implemented with reference to details described above in this disclosure and without limitation. In one or more embodiments, biomedical data 112 may include at least an ECG. In one or more embodiments, biomedical data 112 may include time series data.

With continued reference to FIG. 7, at step 710, method 700 includes receiving, by processor 116 from image capture device 104, image 108 of biomedical data 112. This step may be implemented with reference to details described above in this disclosure and without limitation. In one or more embodiments, receiving image 108 of biomedical data 112 may comprise transforming the image 108 into an in-silicon image 108. In one or more embodiments, receiving image 108 of biomedical data 112 may comprise comparing the biomedical data 112 against at least a quality assurance parameter.

With continued reference to FIG. 7, at step 715, method 700 includes extracting, by processor 116, plurality of biomedical features 124 as a function of biomedical data 112. This step may be implemented with reference to details described above in this disclosure and without limitation. In one or more embodiments, extracting plurality of biomedical features 124 may comprise receiving feature extraction training data 128 comprising plurality of training images as inputs and plurality of training biomedical features as outputs, training feature extraction model 132 by correlating the plurality of training images with the plurality of training biomedical features, and extracting the plurality of biomedical features 124 from image 108 using the trained feature extraction model 132.

With continued reference to FIG. 7, at step 720, method 700 includes receiving, by processor 116, repository data from medical repository 136 as a function of plurality of biomedical features 124. This step may be implemented with reference to details described above in this disclosure and without limitation.

With continued reference to FIG. 7, at step 725, method 700 includes generating, by the processor 116, at least a distance metric 140 as a function of plurality of biomedical features 124 and the repository data. This step may be implemented with reference to details described above in this disclosure and without limitation.

With continued reference to FIG. 7, at step 730, method 700 includes highlighting, by processor 116, at least a biomedical feature 124 within image 108 as a function of at least a distance metric 140. This step may be implemented with reference to details described above in this disclosure and without limitation. In one or more embodiments, highlighting at least a biomedical feature 124 within image 108 may comprise generating a color-coded heat map at one or more regions within the image 108. In one or more embodiments, highlighting at least a biomedical feature 124 within image 108 may comprise receiving, using user interface, user query 164 from user, and highlighting, using the user interface, at least a biomedical feature 124 within the image 108 as a function of the user query 164.

With continued reference to FIG. 7, at step 735, method 700 includes displaying, using display device 160, at least a highlighted biomedical feature 124 within image 108. This step may be implemented with reference to details described above in this disclosure and without limitation.

With continued reference to FIG. 7, in one or more embodiments, method 700 may further comprise identifying, by processor 116, within medical repository 136 at least a second patient associated with at least a similar distance metric 140, wherein a first set of statistical parameters 168 are extracted as a function of image 108, at least a second set of statistical parameters 168 are extracted as a function of at least an image associated with the at least a second patient, and identifying the at least a second patient comprises matching the first set of statistical parameters 168 with the at least a second set of statistical parameters 168 using a statistical model 172.

Figure 8:
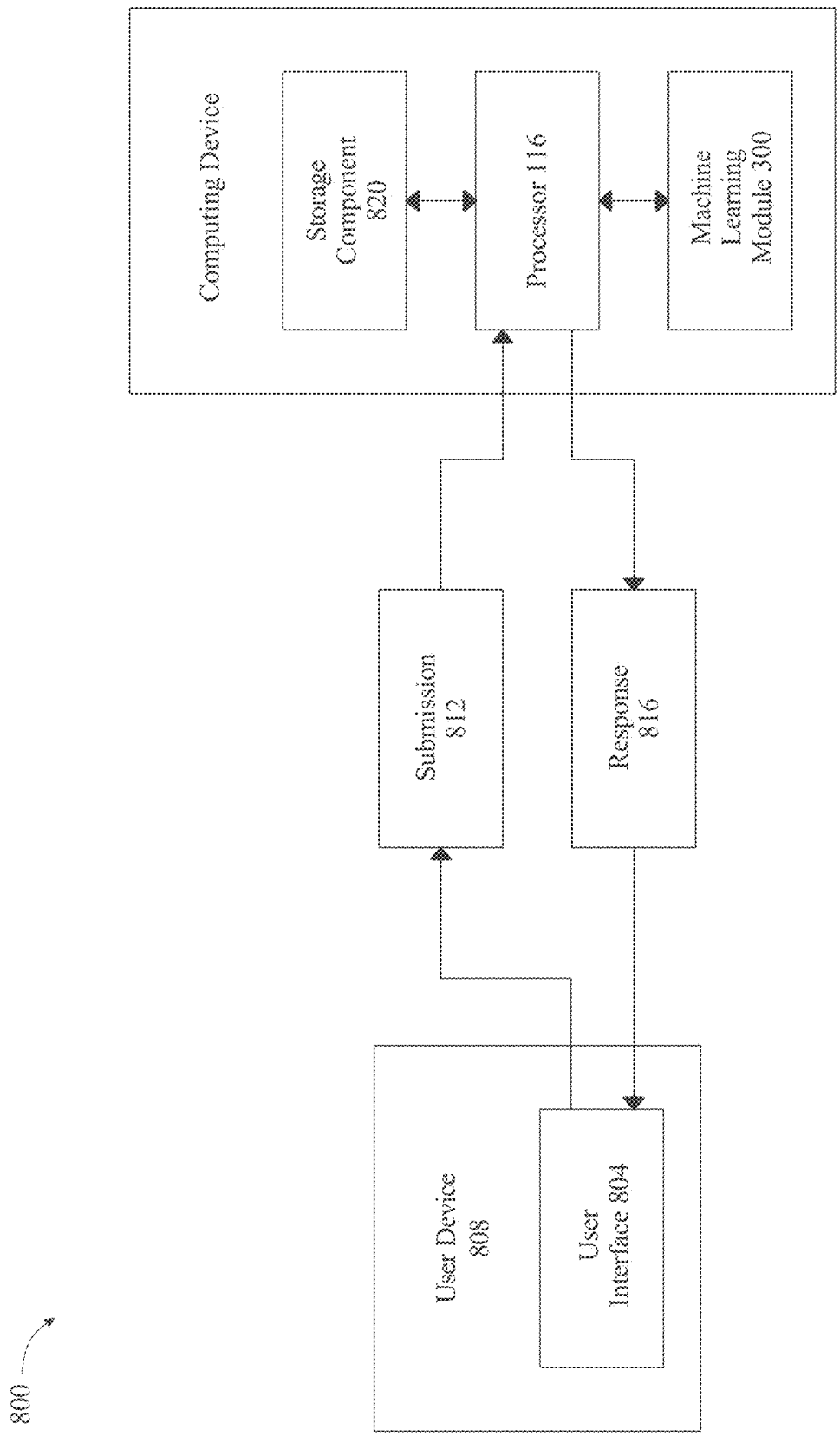
FIG. 8 is an exemplary embodiment of a chatbot system.

Referring now to FIG. 8, in one or more embodiments, apparatus 100 may perform one or more of its functions, such as generating at least a hypothesis 144, by implementing at least a chatbot system 800, an exemplary embodiment of which is schematically illustrated. In one or more embodiments, a user interface 804 may be communicatively connected with a computing device that is configured to operate a chatbot. In some cases, user interface 804 may be local to computing device. Alternatively or additionally, in some other cases, user interface 804 may be remote to computing device, e.g., as part of a user device 808, and communicative with the computing device and processor 116 therein, by way of one or more networks, such as without limitation the internet. Alternatively or additionally, user interface 804 may communicate with user interface 804 and/or computing device using telephonic devices and networks, such as without limitation fax machines, short message service (SMS), or multimedia message service (MMS). Commonly, user interface 804 may communicate with computing device using text-based communication, for example without limitation using a character encoding protocol, such as American Standard for Information Interchange (ASCII). Typically, user interface 804 may conversationally interface a chatbot, by way of at least a submission 812, from the user interface 804 to the chatbot, and a response 816, from the chatbot to the user interface 804. In many cases, one or both of submission 812 and response 816 are text-based communication. Alternatively or additionally, in some cases, one or both of submission 812 and response 816 are audio-based communication.

With continued reference to FIG. 8, submission 812, once received by user interface 804 and/or computing device that operates a chatbot, may be processed by processor 116. In one or more embodiments, processor 116 may process submission 812 using one or more of keyword recognition, pattern matching, and natural language processing. In one or more embodiments, processor 116 may employ real-time learning with evolutionary algorithms. In one or more embodiments, processor 116 may retrieve a pre-prepared response from at least a storage component 820, based upon submission 812. Alternatively or additionally, in one or more embodiments, processor 116 may communicate a response 816 without first receiving a submission 812, thereby initiating a conversation. In some cases, processor 116 may communicate an inquiry to user interface 804 and/or computing device, wherein processor 116 is configured to process an answer to the inquiry in a following submission 812 from the user interface 804 and/or computing device. In some cases, an answer to an inquiry presented within submission 812 from user device 804 and/or computing device may be used by the computing device as an input to another function.

Figure 9A:
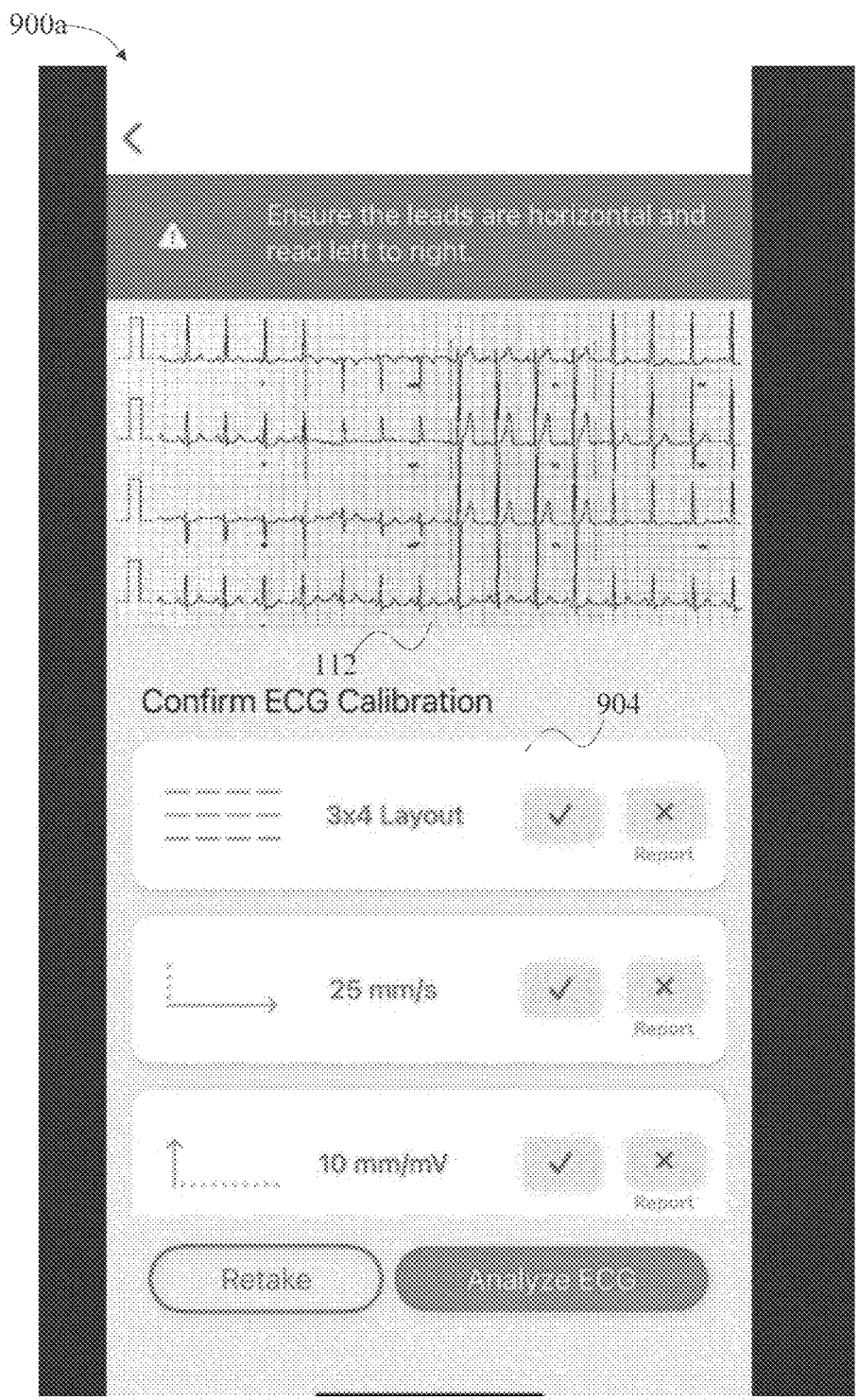
FIG. 9A-K are exemplary embodiments of user interfaces.
Figure 9B:
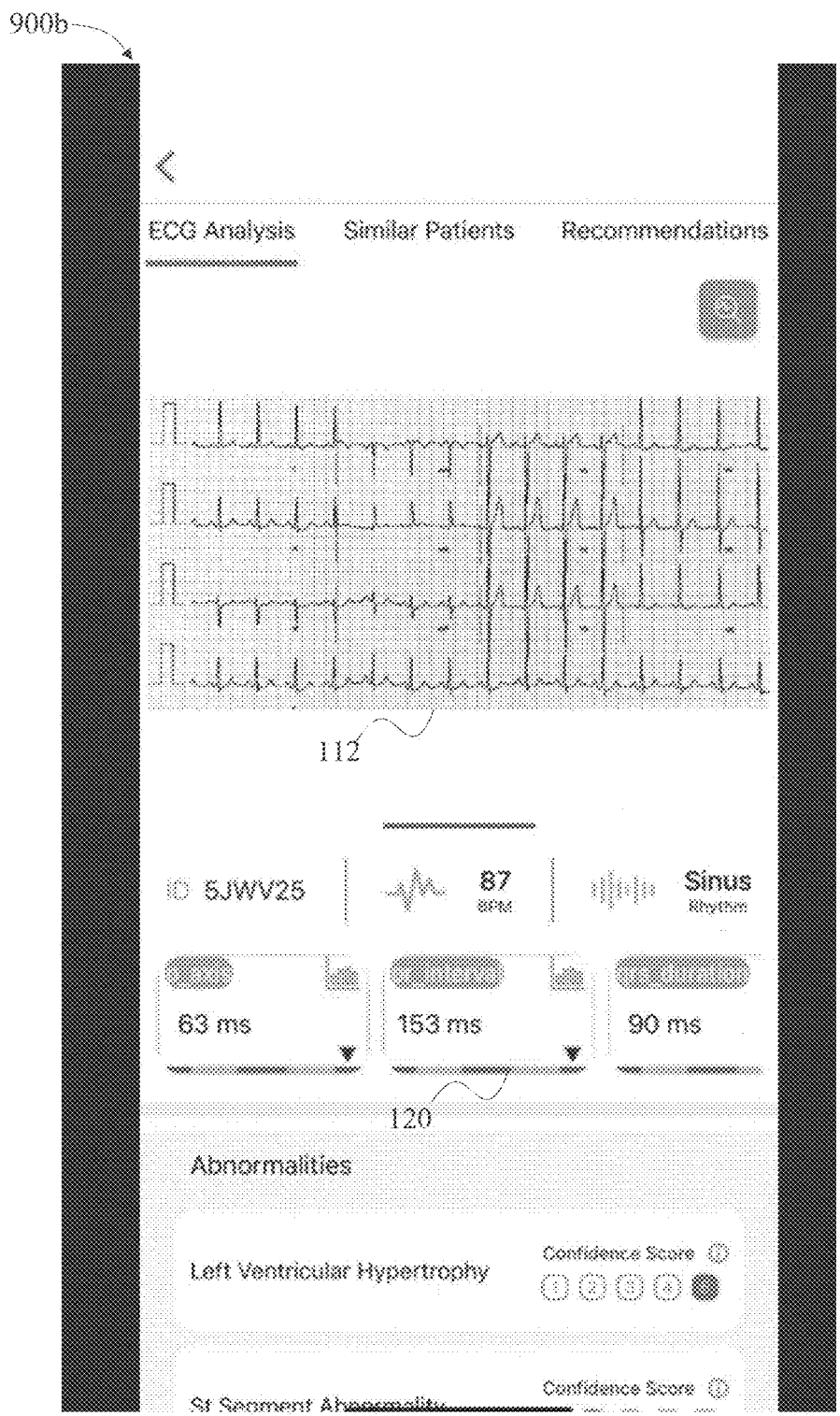
Figure 9C:
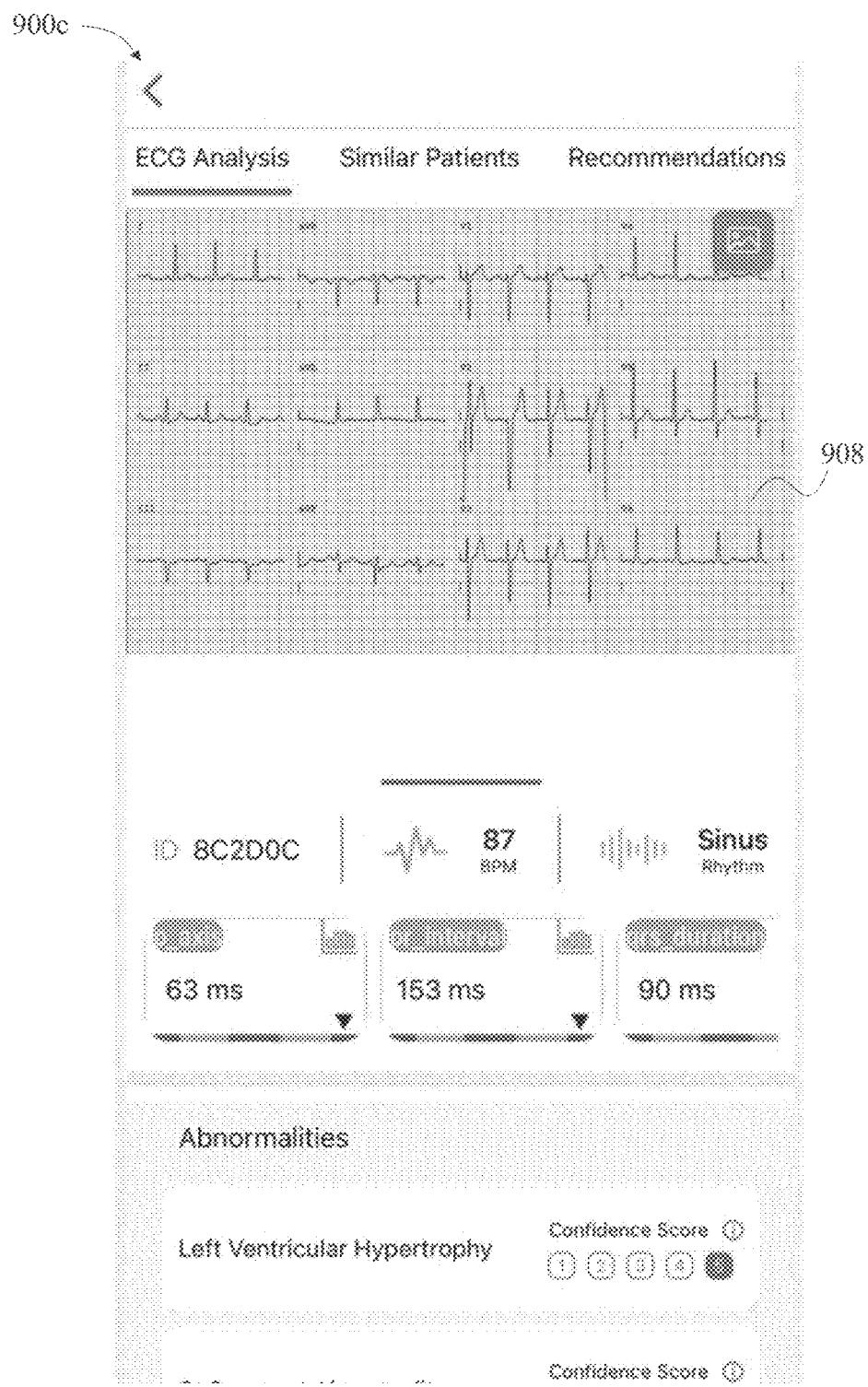
Figure 9D:
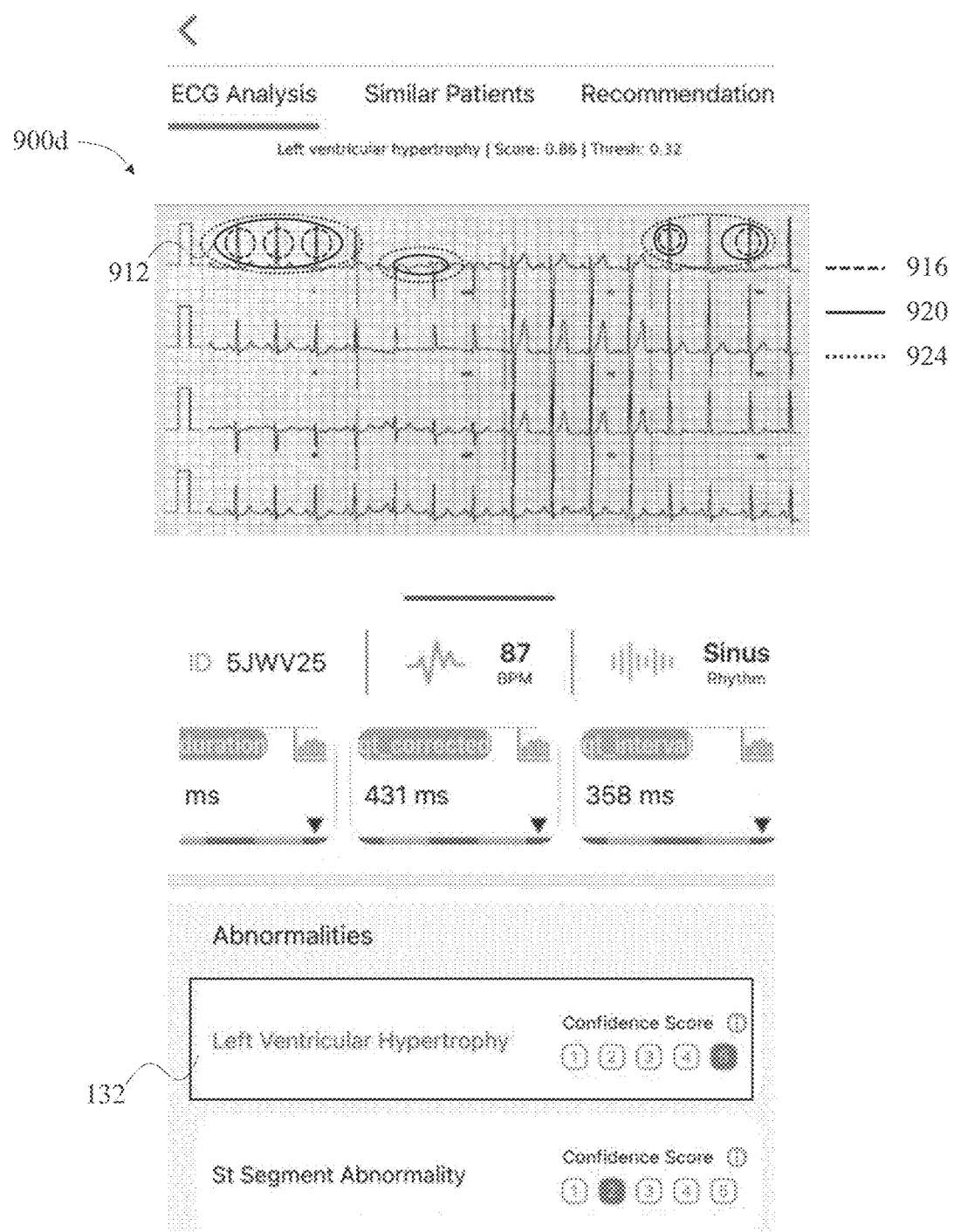

Referring now to FIG. 9A-K, exemplary user interfaces 900a-k are included to collectively illustrate a nonlimiting example for implementing apparatus 100. All exemplary screenshots are captured from a mobile device. FIG. 9A includes a image 108 of an ECG 200, wherein user is prompted to perform one or more calibrations 904 for the ECG 200 before initiating subsequent steps. This image 108 serves as a basis in all subsequent exemplary screenshots. FIG. 9B includes the same ECG 200 in FIG. 9A post calibration, wherein a plurality of biomedical features 124, such as p_axis, pr_interval, and qrs_duration, is extracted from the ECG 200 following procedures described above in this disclosure. FIG. 9C includes the same ECG as FIG. 9B upon converting it into an in-silicon image 908.

Figure 9E:
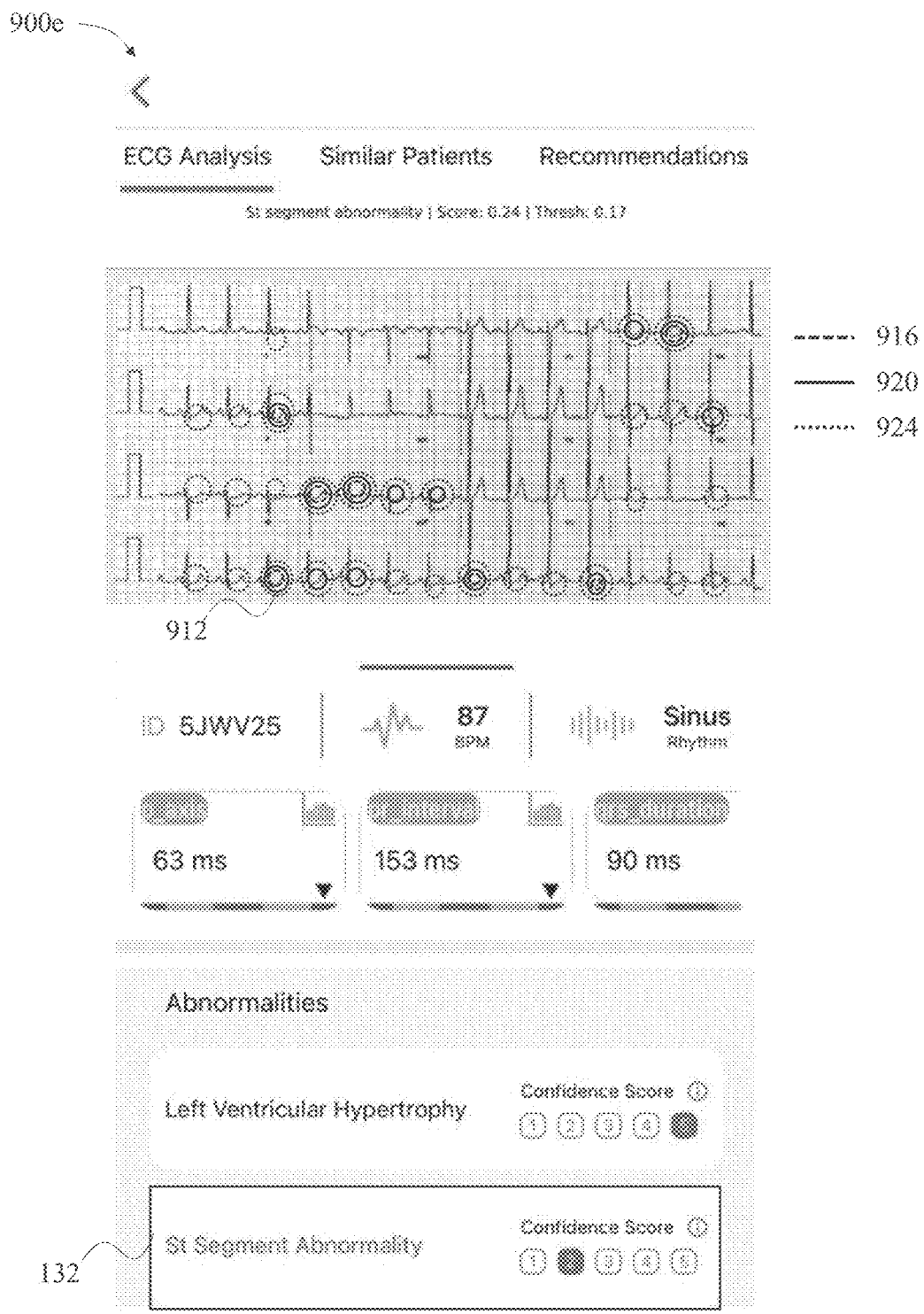
Figure 9F:
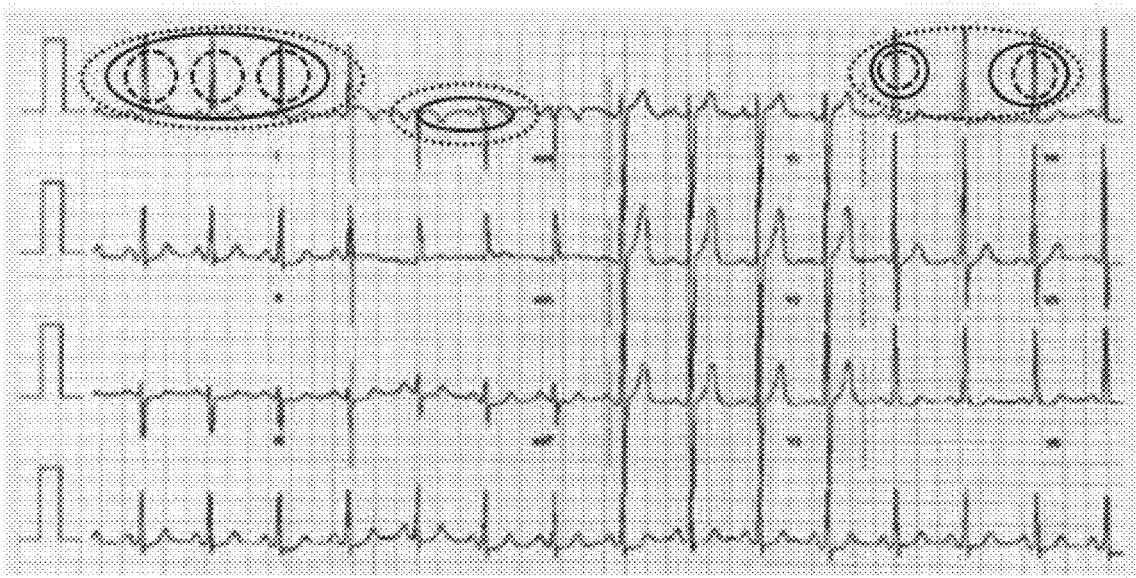
Figure 9G:
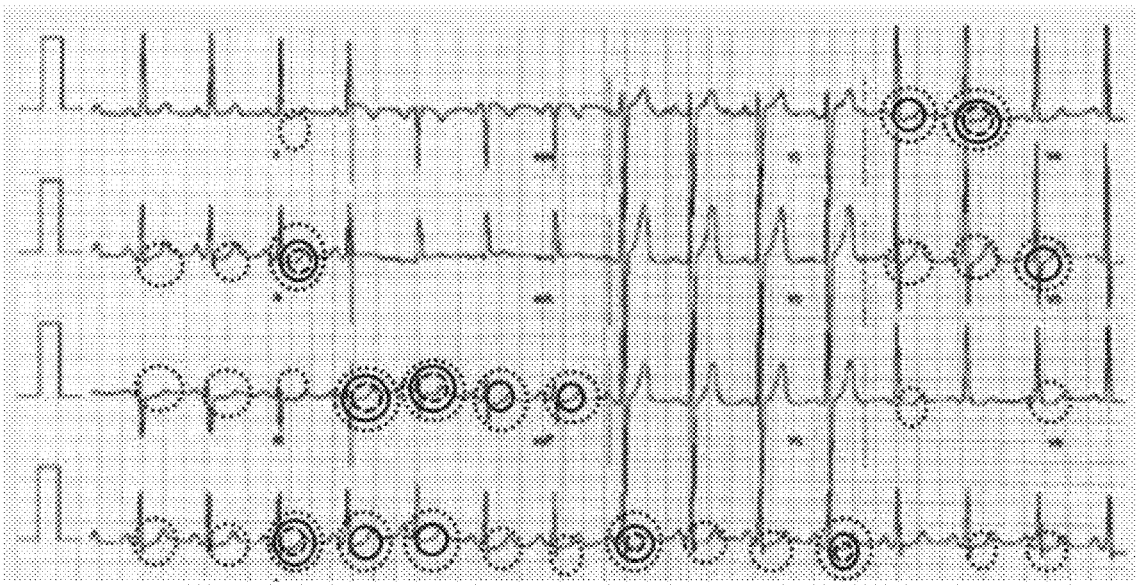
Figure 9H:
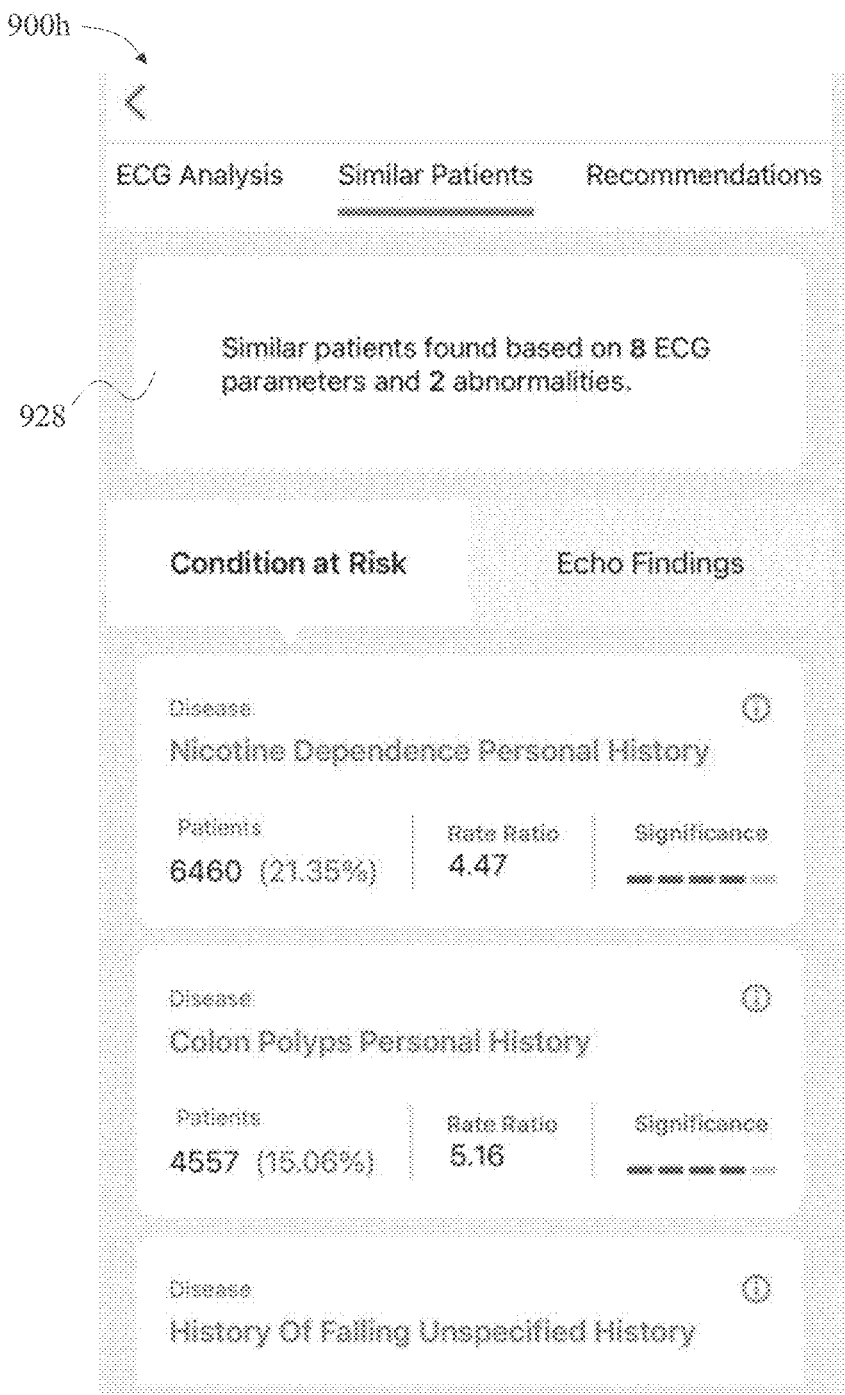
Figure 9I:
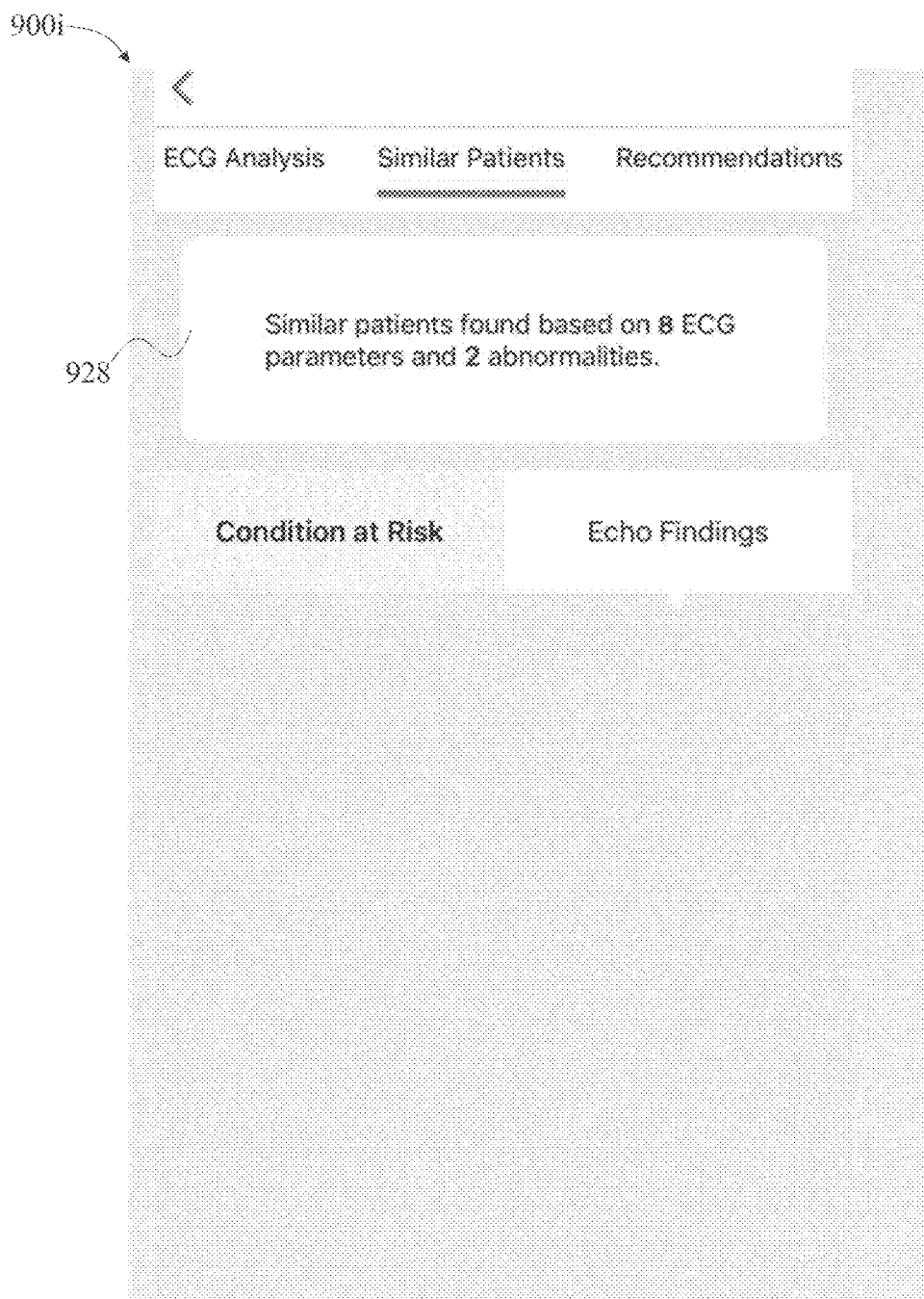

With continued reference to FIG. 9A-K, FIG. 9D includes a hypothesis 144, left ventricular hypertrophy, generated as a function of plurality of biomedical features 124 and validated with a 5/5 confidence score. Additionally, FIG. 9D includes a representation of a color-coded heat map 912 generated at a plurality of regions within image 108, wherein dashed line 916 marks a first color (e.g., red), solid line 920 marks a second color (i.e., yellow) different from the first color, and dotted line 924 marks a third color (e.g., green) that is different from both the first color and the second color. It is worth noting that these cutoffs between colors may be defined arbitrarily, as color-coded heat map 912 may contain a continuum of a plurality of colors instead. These color-coded regions highlight a plurality of abnormal biomedical features within biomedical data (ECG) as a function of their relevance to hypothesis 144. FIG. 9E includes a different hypothesis 144, ST segment abnormality, generated as a function of plurality of biomedical features 124 and validated with a 2/5 confidence score. Additionally, FIG. 9E includes a representation of a different color-coded heat map 912 generated at a different plurality of regions within image 108, following the same protocols described above for FIG. 9D. FIG. 9F and FIG. 9G contain the same color-coded heat map as FIG. 9D and FIG. 9E, respectively, which are zoomed in to show additional details therein.

Figure 9J:
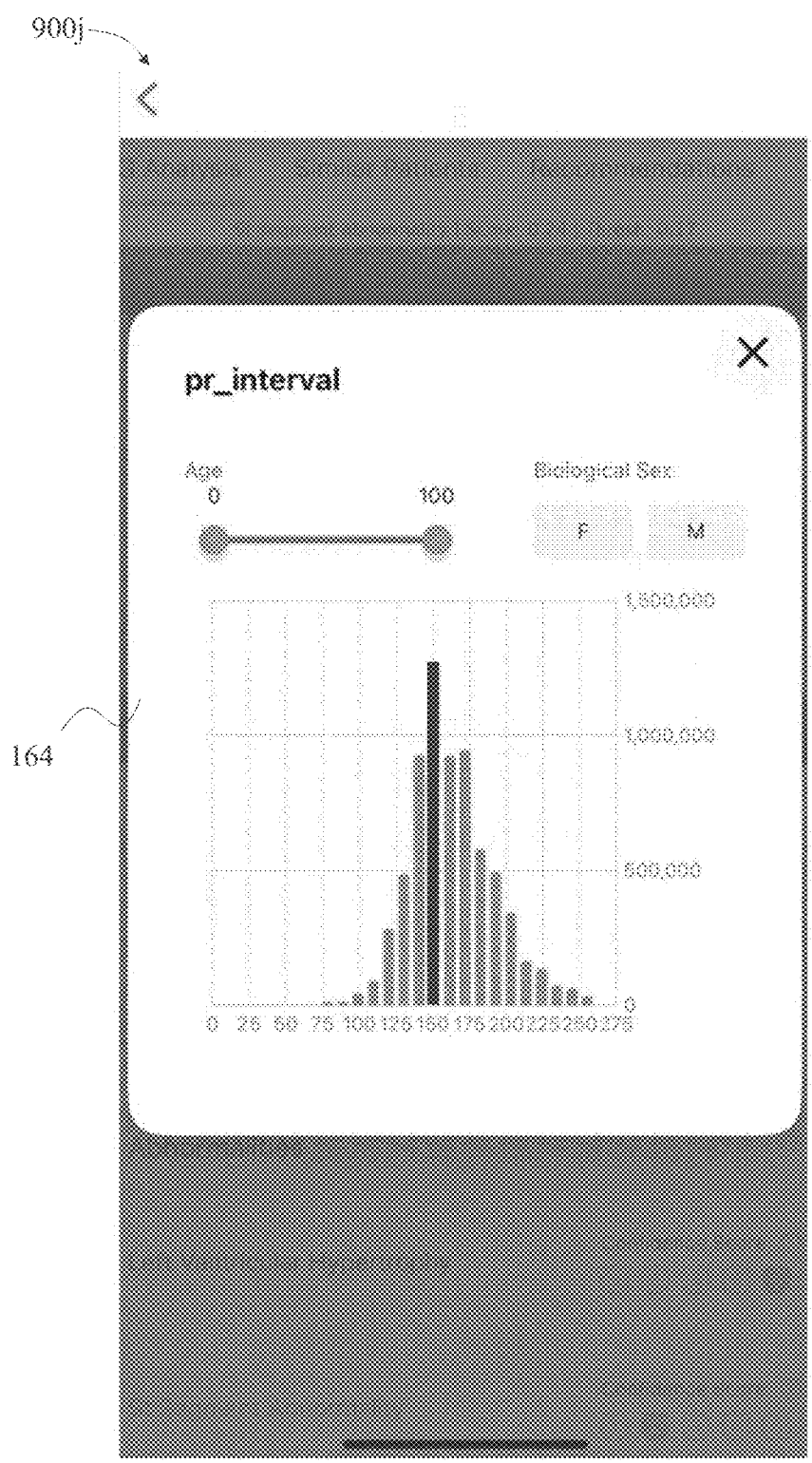
Figure 9K:
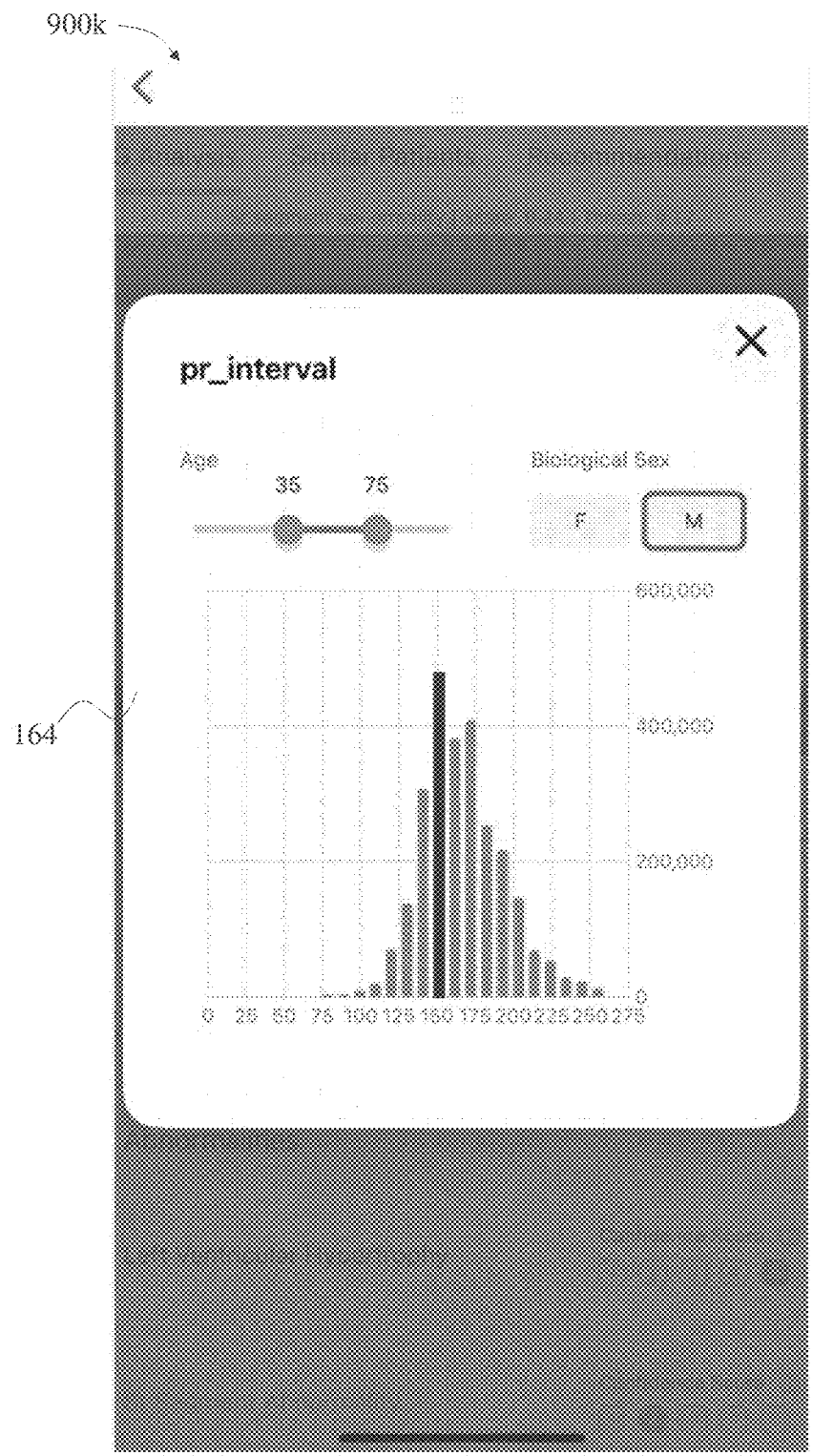

With continued reference to FIG. 9A-K, FIG. 9H-I include additional features of apparatus 100 wherein similar patients 928 are identified as a function of image 108 with conditions, such as nicotine dependence and colon polyps, related thereto. FIG. 9J includes an exemplary biomedical feature 124, pr_interval, positioned within a statistical model 172 (i.e., a histogram), wherein the statistical model 172 is built as a function of a cohort of patients; FIG. 9K reflects the same information as FIG. 9J upon filtering the same cohort of patients to a sub-cohort of female patients aged between 35 and 75 years old.

Figure 10:
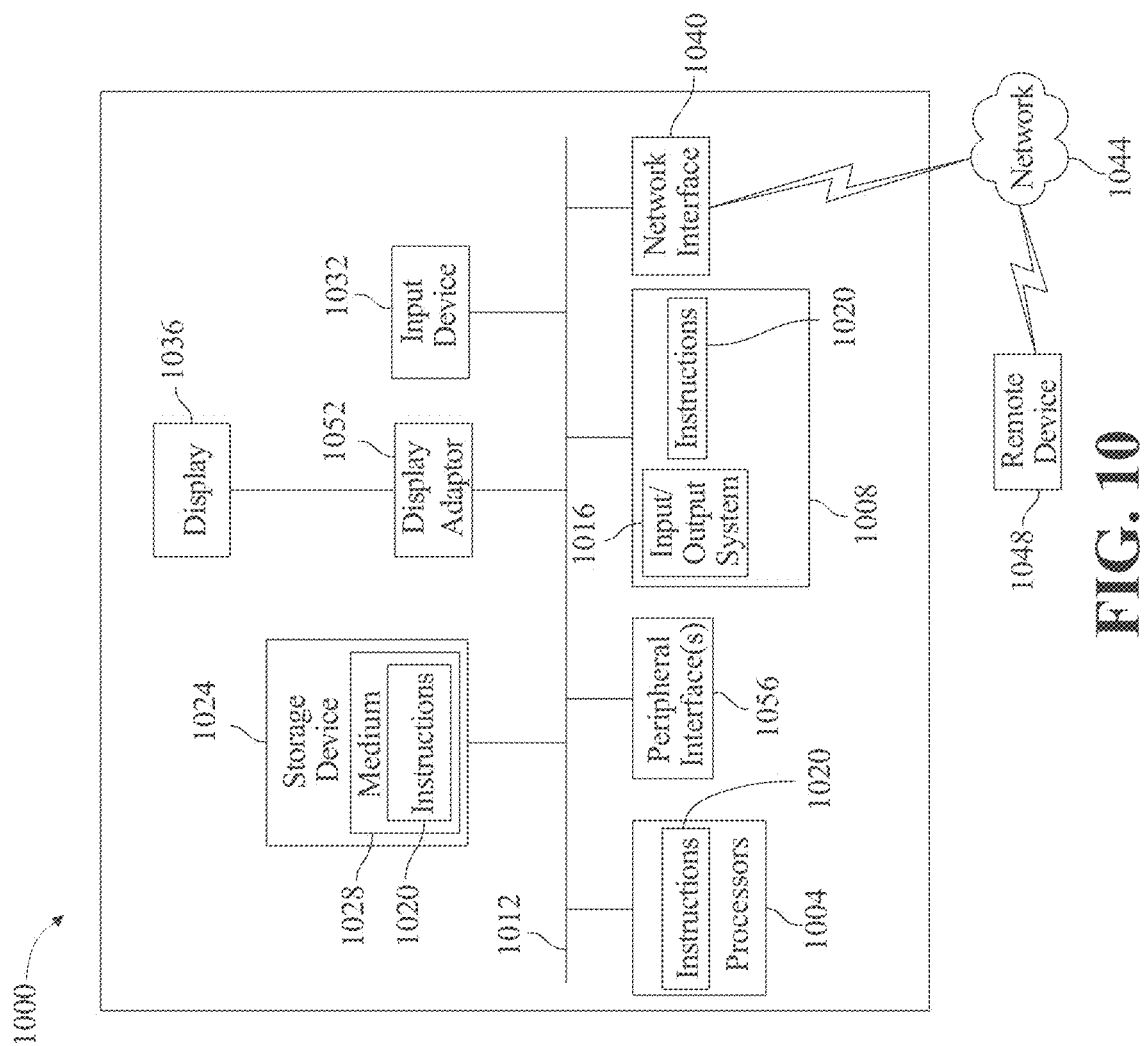
FIG. 10 is a block diagram of an exemplary embodiment of a computing system that can be used to implement any one or more of the methodologies disclosed herein and any one or more portions thereof.

Referring now to FIG. 10, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 10, the figure shows a diagrammatic representation of one embodiment of a computing device in the exemplary form of a computing system 1000 within which a set of instructions for causing the computing system 1000 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 1000 may include a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures. Processor 1004 may include any suitable processor, such as without limitation a processor incorporating logical circuitry for performing arithmetic and logical operations, such as an arithmetic and logic unit, which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 10, memory 1008 may include various components (e.g., machine-readable media) including, but not limited to, a random-access memory component, a read only component, and any combinations thereof. In one example, a basic input/output system 1016, including basic routines that help to transfer information between elements within computing system 1000, such as during start-up, may be stored in memory 1008. Memory 1008 (e.g., stored on one or more machine-readable media) may also include instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

With continued reference to FIG. 10, computing system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 1024 (or one or more components thereof) may be removably interfaced with computing system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computing system 1000. In one example, software 1020 may reside, completely or partially, within machine-readable medium 1028. In another example, software 1020 may reside, completely or partially, within processor 1004.

With continued reference to FIG. 10, computing system 1000 may also include an input device 1032. In one example, a user of computing system 1000 may enter commands and/or other information into computing system 1000 via input device 1032. Examples of input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

With continued reference to FIG. 10, user may also input commands and/or other information to computing system 1000 via storage device 1024 (e.g., a removable disk drive, a flash drive, etc.) and/or network interface device 1040. A network interface device, such as network interface device 1040, may be utilized for connecting computing system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or wireless mode of communication. In general, any network topology may be used. Information (e.g., data, software 1020, etc.) may be communicated to and/or from computing system 1000 via network interface device 1040.

With continued reference to FIG. 10, computing system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computing system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for identifying at least one abnormal biomedical feature within at least one image of biomedical data, the apparatus comprising:
   an image capture device configured to capture the at least one image of biomedical data pertaining to a first patient;
   a processor communicatively connected to the image capture device;
   a memory communicatively connected to the processor, wherein the memory contains instructions configuring the processor to:
   receive the at least one image of biomedical data from the image capture device;
   extract a plurality of biomedical features from the biomedical data;
   receive repository data from a medical repository as a function of the plurality of biomedical features;

generate at least one distance metric as a function of the plurality of biomedical features and the repository data;

highlight the at least one abnormal biomedical feature within the at least one image as a function of the at least one distance metric;

identify within the medical repository at least one second patient associated with at least one similar distance metric, wherein:

a first set of statistical parameters are extracted as a function of the at least one image, and at least one second set of statistical parameters are extracted as a function of at least one image associated with the at least one second patient; and identifying the at least one second patient comprises matching the first set of statistical parameters with the at least one second set of statistical parameters using a statistical model; and a display device communicatively connected to the processor, wherein the display device is configured to display the at least one highlighted abnormal biomedical feature within the at least one image.

2. The apparatus of claim 1, wherein generating the at least one distance metric comprises:

generating a plurality of hypotheses by creating a plurality of labels, wherein each label of the plurality of labels represents a diagnostic feature associated with one or more hypotheses within the plurality of hypotheses;

identifying at least one hypothesis from the plurality of hypotheses by matching the at least one abnormal biomedical feature of the plurality of biomedical features against at least a label of the plurality of labels; and generating the at least one distance metric as a function of the at least one hypothesis.

3. The apparatus of claim 1, wherein:

the biomedical data includes at least one electrocardiogram (ECG); and the at least one abnormal biomedical feature includes at least one ECG feature identified from the at least one ECG.

4. The apparatus of claim 1, wherein:

the biomedical data includes time series data; and the at least one abnormal biomedical feature includes at least one feature identified from the time series data.

5. The apparatus of claim 1, wherein extracting the plurality of biomedical features comprises:

receiving feature extraction training data comprising a plurality of training images as inputs and a plurality of training biomedical features as outputs;

training a feature extraction model by correlating the plurality of training images with the plurality of training biomedical features; and extracting the plurality of biomedical features from the image using the trained feature extraction model.

6. The apparatus of claim 1, wherein receiving the at least one image of biomedical data comprises:

extracting a plurality of biomedical parameters from the at least one image of biomedical data;

converting the plurality of biomedical parameters to one or more digitized signals; and transforming the one or more digitized signals into an in-silicon image.

7. The apparatus of claim 6, wherein receiving the at least one image of biomedical data further comprises:

validating the one or more digitized signals, comprising:

classifying the one or more digitized signals to a plurality of preliminary parameters; and determining an accuracy status of the plurality biomedical parameters by comparing the plurality of preliminary parameters to the plurality of biomedical parameters; and generating a quality diagnostic of the biomedical data based on a result of the validation.

8. The apparatus of claim 1, wherein highlighting the at least one abnormal biomedical feature within the at least one image comprises generating a color-coded heat map at one or more regions within the at least one image.

9. The apparatus of claim 8, wherein generating the color-coded heat map comprises:

generating a plurality of color-coded regions as a function of the at least one distance metric; and displaying, using the display device, the plurality of color-coded regions.

10. The apparatus of claim 1, further comprising a user interface, wherein highlighting the at least one abnormal biomedical feature within the at least one image comprises:

receiving, using the user interface, a user query from a user; and highlighting, using the user interface, the at least one abnormal biomedical feature within the at least one image as a function of the user query.

11. A method for identifying at least one abnormal biomedical feature within at least one image of biomedical data, the method comprising:

capturing, using an image capture device, the at least one image of biomedical data pertaining to a first patient;

receiving, by a processor from the image capture device, the at least one image of biomedical data;

extracting, by the processor, a plurality of biomedical features as a function of the biomedical data;

receiving, by the processor, repository data from a medical repository as a function of the plurality of biomedical features;

generating, by the processor, at least one distance metric as a function of the plurality of biomedical features and the repository data;

highlighting, by the processor, the at least one abnormal biomedical feature within the at least one image as a function of the at least one distance metric;

identifying, by the processor, within the medical repository at least one second patient associated with at least one similar distance metric, wherein:

a first set of statistical parameters are extracted as a function of the at least one image, and at least one second set of statistical parameters are extracted as a function of at least one image associated with the at least one second patient; and identifying the at least one second patient comprises matching the first set of statistical parameters with the at least one second set of statistical parameters using a statistical model; and displaying, using a display device, the at least one highlighted abnormal biomedical feature within the at least one image.

12. The method of claim 11, wherein generating the at least one distance metric comprises:

generating a plurality of hypotheses by creating a plurality of labels, wherein each label of the plurality of labels represents a diagnostic feature associated with one or more hypotheses within the plurality of hypotheses;

identifying at least one hypothesis from the plurality of hypotheses by matching the at least one abnormal biomedical feature of the plurality of biomedical features against at least a label of the plurality of labels; and generating the at least one distance metric as a function of the at least one hypothesis.

13. The method of claim 11, wherein:
the biomedical data includes at least one electrocardiogram (ECG); and
the at least one abnormal biomedical feature includes at least one ECG feature identified from the at least one ECG.

14. The method of claim 11, wherein:
the biomedical data includes time series data; and
the at least one abnormal biomedical feature includes at least one feature identified from the time series data.

15. The method of claim 11, wherein extracting the plurality of biomedical features comprises:
receiving feature extraction training data comprising a plurality of training images as inputs and a plurality of training biomedical features as outputs;
training a feature extraction model by correlating the plurality of training images with the plurality of training biomedical features; and
extracting the plurality of biomedical features from the image using the trained feature extraction model.

16. The method of claim 11, wherein receiving the at least one image of biomedical data comprises:
extracting a plurality of biomedical parameters from the at least one image of biomedical data;
converting the plurality of biomedical parameters to one or more digitized signals; and
transforming the one or more digitized signals into an in-silicon image.

17. The method of claim 16, wherein receiving the at least one image of biomedical data further comprises:
validating the one or more digitized signals, comprising:
classifying the one or more digitized signals to a plurality of preliminary parameters; and
determining an accuracy status of the plurality biomedical parameters by comparing the plurality of preliminary parameters to the plurality of biomedical parameters; and
generating a quality diagnostic of the biomedical data based on a result of the validation.

18. The method of claim 11, wherein highlighting the at least one abnormal biomedical feature within the at least one image comprises generating a color-coded heat map at one or more regions within the at least one image.

19. The method of claim 18, wherein generating the color-coded heat map comprises:
generating a plurality of color-coded regions as a function of the at least one distance metric; and
displaying, using the display device, the plurality of color-coded regions.

20. The method of claim 11, wherein highlighting the at least one abnormal biomedical feature within the at least one image comprises:
receiving, using a user interface, a user query from a user; and
highlighting, using the user interface, the at least one abnormal biomedical feature within the at least one image as a function of the user query.

* * * * *